United States Patent
Ceballos Lentini et al.

(10) Patent No.: US 11,393,575 B1
(45) Date of Patent: Jul. 19, 2022

(54) SYSTEMS AND METHODS TO PROCESS ELECTRONIC IMAGES FOR SYNTHETIC IMAGE GENERATION

(71) Applicant: PAIGE.AI, Inc., New York, NY (US)

(72) Inventors: Rodrigo Ceballos Lentini, Flemington, NJ (US); Christopher Kanan, Pittsford, NY (US)

(73) Assignee: PAIGE.AI, Inc., New York, NY (US)

( * ) Notice: Subject to any disclaimer, the term of this patent is extended or adjusted under 35 U.S.C. 154(b) by 0 days.

(21) Appl. No.: 17/645,296

(22) Filed: Dec. 20, 2021

Related U.S. Application Data

(63) Continuation of application No. 17/645,197, filed on Dec. 20, 2021.

(Continued)

(51) Int. Cl.
*G16H 30/20* (2018.01)
*G16H 30/40* (2018.01)
(Continued)

(52) U.S. Cl.
CPC ............. *G16H 30/20* (2018.01); *G06N 20/00* (2019.01); *G06T 7/0012* (2013.01); *G16H 30/40* (2018.01); *G16H 50/50* (2018.01); *G06T 2207/20081* (2013.01); *G06T 2207/20212* (2013.01); *G06T 2207/30004* (2013.01)

(58) Field of Classification Search
CPC ........ G16H 30/20; G16H 30/40; G16H 50/50; G06N 20/00; G06T 7/0012; G06T 2207/20081; G06T 2207/20212; G06T 2207/30004
See application file for complete search history.

(56) References Cited

U.S. PATENT DOCUMENTS

2018/0307947 A1   10/2018  Choi et al.
2019/0066281 A1*  2/2019  Zheng ................. G06T 5/006
(Continued)

OTHER PUBLICATIONS

Segal et al., "Evaluating the Clinical Realism of Synthetic Chest X-Rays Generated Using Progressively Growing GANs", arXiv:2010.03975v2, Mar. 10, 2021, pp. 1-18 (Year: 2021).*
(Continued)

*Primary Examiner* — Nay A Maung
*Assistant Examiner* — Jose M Torres
(74) *Attorney, Agent, or Firm* — Bookoff McAndrews, PLLC

(57) ABSTRACT

Systems and methods are disclosed for generating synthetic medical images, including images presenting rare conditions or morphologies for which sufficient data may be unavailable. In one aspect, style transfer methods may be used. For example, a target medical image, a segmentation mask identifying style(s) to be transferred to area(s) of the target, and source medical image(s) including the style(s) may be received. Using the mask, the target may be divided into tile(s) corresponding to the area(s) and input to a trained machine learning system. For each tile, gradients associated with a content and style of the tile may be output by the system. Pixel(s) of at least one tile of the target may be altered based on the gradients to maintain content of the target while transferring the style(s) of the source(s) to the target. The synthetic medical image may be generated from the target based on the altering.

20 Claims, 17 Drawing Sheets

Related U.S. Application Data

(60) Provisional application No. 63/203,036, filed on Jul. 6, 2021.

(51) Int. Cl.
G06N 20/00 (2019.01)
G16H 50/50 (2018.01)
G06T 7/00 (2017.01)

(56) References Cited

U.S. PATENT DOCUMENTS

| | | | | |
|---|---|---|---|---|
| 2019/0370969 | A1* | 12/2019 | Katzmann | G06N 3/0454 |
| 2020/0364864 | A1* | 11/2020 | Shanbhag | G06T 7/0014 |
| 2020/0394459 | A1* | 12/2020 | Xu | G06K 9/6256 |
| 2021/0249142 | A1* | 8/2021 | Lau | G16H 30/40 |
| 2021/0397972 | A1* | 12/2021 | Walters | G06N 3/0445 |

OTHER PUBLICATIONS

Togo et al., "Synthetic Gastritis Image Generation via Loss Function-Based Conditional PGGAN", IEEE Access, vol. 7, Jul. 1, 2019, pp. 87448-87457 (Year: 2019).*

Salehinejad et al., "Synthesizing Chest X-Ray Pathology for Training Deep Convolutional Neural Networks", IEEE Transactions on Medical Imaging, vol. 38, No. 5, May 2019, pp. 1197-1206 (Year: 2019).*

Madani et al., "Chest x-ray generation and data augmentation for cardiovascular abnormality classification", Proc. SPIE 10574, Medical Imaging 2018: Image Processing, 105741M (Mar. 2, 2018), pp. 105741M-1-105741M-6 (Year: 2018).*

Guibas et al., "Synthetic Medical Images from Dual Generative Adversarial Networks", arXiv:1709.01872v3, Jan. 8, 2018, pp. 1-9 (Year: 2018).

Islam et al., "GAN-based synthetic brain PET image generation", Brain Inform. 2020;7(1):3, Mar. 30, 2020, pp. 1-12 (Year: 2020).

Campanella et al., Clinical-grade computational pathology using weakly supervised deep learning on whole slide images, Nature Medicine, Aug. 2019, 25(8): 1301-1309, https://www.ncbi.nlm.nih.gov/pmc/articles/PMC7418463/pdf/nihms-1609511.pdf [retrieved on Dec. 20, 2021]. Retrieved from the Internet (33 pages).

Park et al., Semantic Image Synthesis with Spatially-Adaptive Normalization, CVPR 2019, Jun. 18, 2019, https://openaccess.thecvf.com/content_CVPR_2019/papers/Park_Semantic_Image_Synthesis_With_Spatially-Adaptive_Normalization_CVPR_2019_paper.pdf [retrieved on Dec. 20, 2021]. Retrieved from the Internet (10 pages).

Campanella et al., Terabyte-scale Deep Multiple Instance Learning for Classification and Localization in Pathology, arXiv, May 17, 2018, https://arxiv.org/pdf/1805.06983.pdf [retrieved on Dec. 20, 2021]. Retrieved from the Internet (17 pages).

* cited by examiner

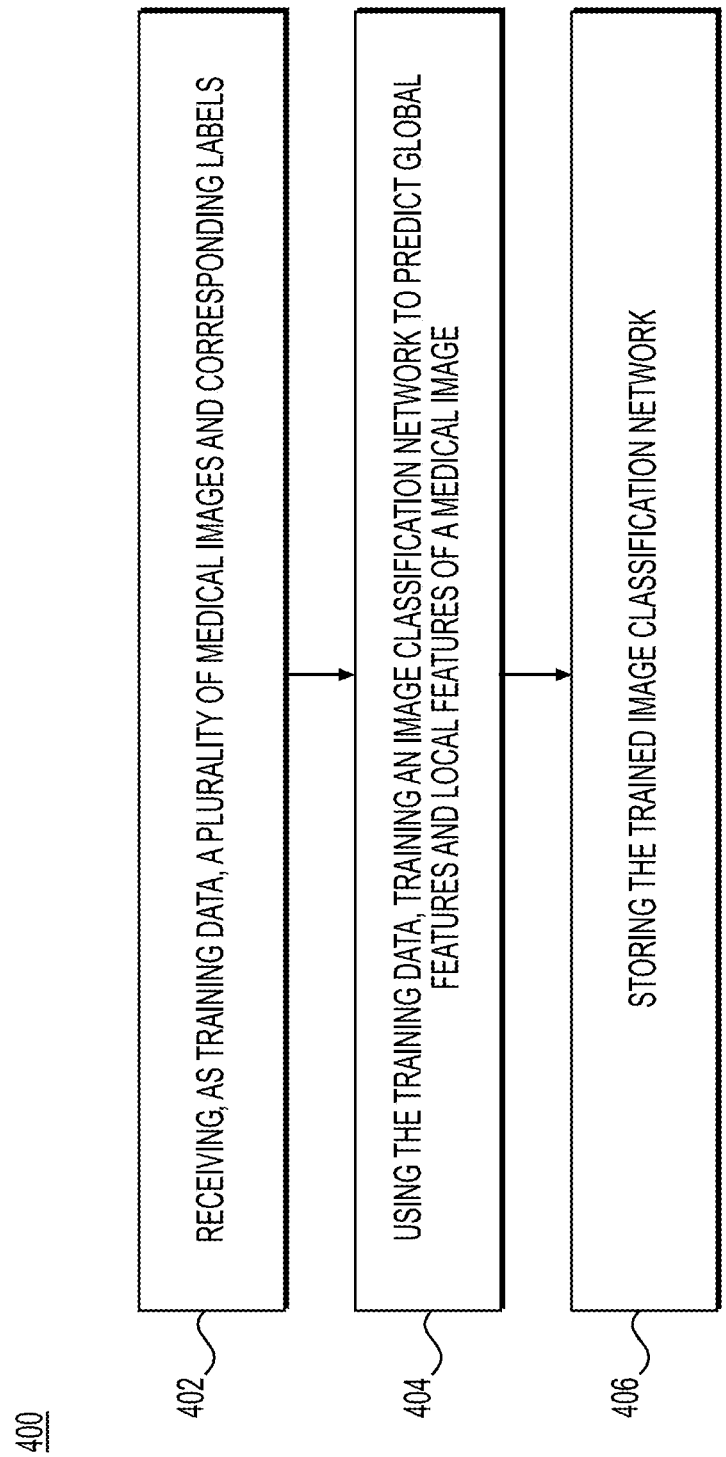

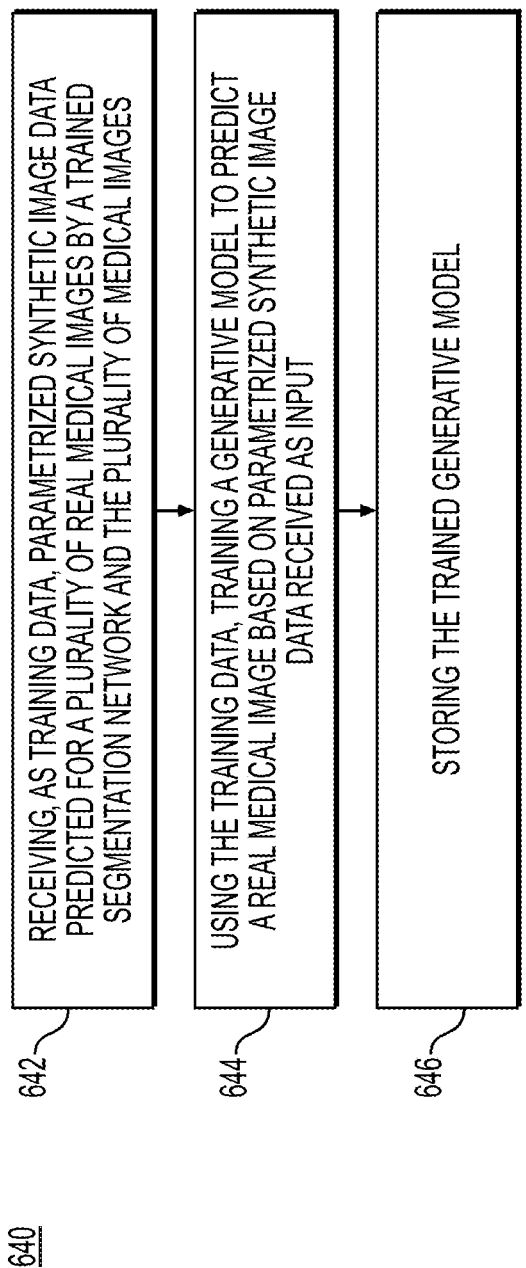

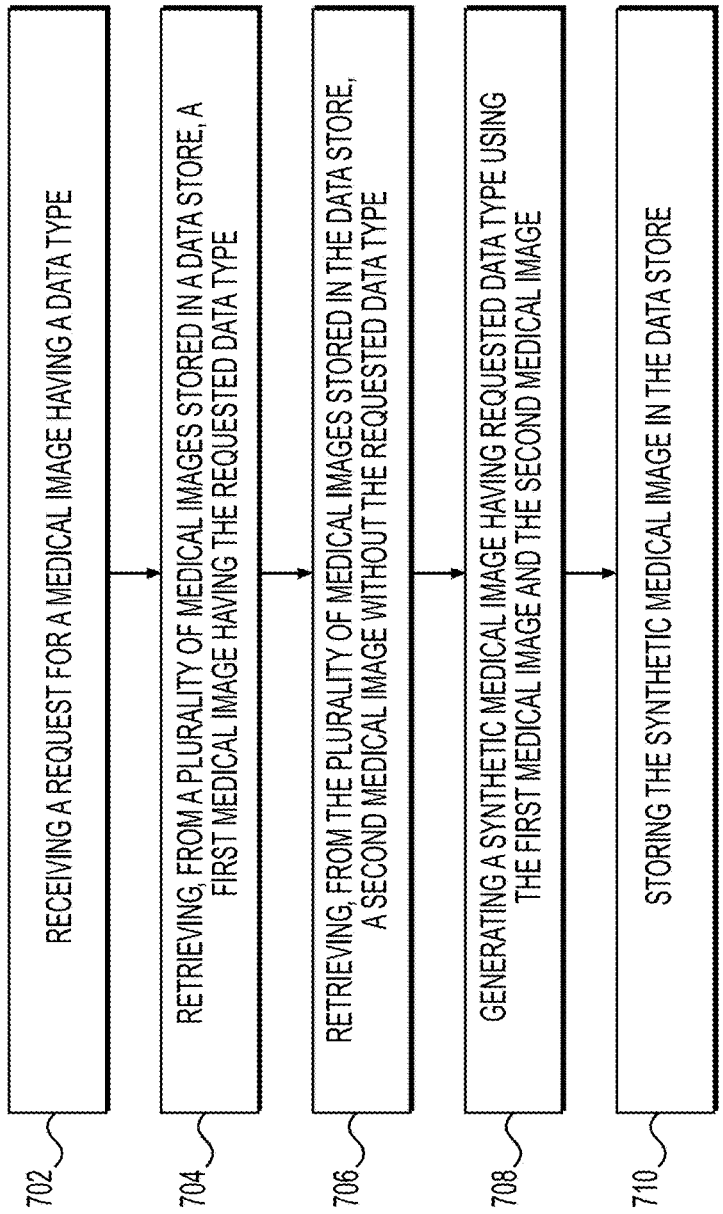

SYSTEMS AND METHODS TO PROCESS ELECTRONIC IMAGES FOR SYNTHETIC IMAGE GENERATION

RELATED APPLICATION(S)

This application is a continuation of and claims priority to U.S. Non-provisional patent application Ser. No. 17/645,197 filed on Dec. 20, 2021, which claims priority to U.S. Provisional Application No. 63/203,036 filed Jul. 6, 2021, the entire disclosures of which are hereby incorporated by reference in their entireties.

FIELD OF THE DISCLOSURE

Various aspects of the present disclosure pertain generally to image processing methods. More specifically, particular aspects of the present disclosure relate to systems and methods for using machine learning and/or image composition methods to synthesize and/or combine medical images with desired characteristics.

BACKGROUND

In biology, exceptions are common. For example, many cancers are rare cancers. This makes it difficult to train medical professionals or artificial intelligence (AI) systems to diagnose rare conditions because they do not see enough real-world variability during learning. For example, for prostate cancer presentations, it may be rare to see Gleason grade 5 (e.g., high-grade prostate cancer) simultaneously with atrophy and multiple treatment effects (e.g., radiation and hormone depriving drugs). Seeing variability during learning may be important to ensure the right patterns are learned by AI systems or by medical professionals.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for using machine learning and/or image composition methods to synthesize and/or combine medical images with desired characteristics (e.g., requested data types).

A system for generating a synthetic medical image using style transfer includes a processor, and a memory coupled to the processor and storing instructions that, when executed by the processor, cause the system to perform operations. The operations may include receiving a target medical image, receiving a segmentation mask identifying one or more styles to be transferred to one or more areas of the target medical image, and receiving one or more source medical images including the one or more styles identified in the segmentation mask. The operations may also include dividing the target medical image into one or more tiles corresponding to the one or more areas using the segmentation mask, providing the one or more tiles as input to a trained machine learning system, and receiving, for each of the one or more tiles, gradients associated with a content and a style of the respective tile as output of the trained machine learning system. The operations may further include altering one or more pixels of at least one of the one or more tiles of the target medical image based on the gradients to maintain content of the target medical image while transferring the one or more styles of the one or more source medical images to the target medical image, and generating the synthetic medical image from the target medical image based on the altering.

A method for generating a synthetic medical image using style transfer may include receiving a target medical image, receiving a segmentation mask identifying one or more styles to be transferred to one or more areas of the target medical image, and receiving one or more source medical images including the one or more styles identified in the segmentation mask. The method may also include dividing the target medical image into one or more tiles corresponding to the one or more areas using the segmentation mask, providing the one or more tiles as input to a trained machine learning system, and receiving, for each of the one or more tiles, gradients associated with a content and a style of the respective tile as output of the trained machine learning system. The method may further include altering one or more pixels of at least one of the one or more tiles of the target medical image based on the gradients to maintain content of the target medical image while transferring the one or more styles of the one or more source medical images to the target medical image, and generating the synthetic medical image from the target medical image based on the altering.

A non-transitory computer-readable medium storing instructions that, when executed by a processor, cause the processor to perform operations for generating a synthetic image using style transfer, the operations including receiving a target medical image, receiving a segmentation mask identifying one or more styles to be transferred to one or more areas of the target medical image, and receiving one or more source medical images including the one or more styles identified in the segmentation mask. The operations may also include dividing the target medical image into one or more tiles corresponding to the one or more areas using the segmentation mask, providing the one or more tiles as input to a trained machine learning system, and receiving, for each of the one or more tiles, gradients associated with a content and a style of the respective tile as output of the trained machine learning system. The operations may further include altering one or more pixels of at least one of the one or more tiles of the target medical image based on the gradients to maintain content of the target medical image while transferring the one or more styles of the one or more source medical images to the target medical image, and generating the synthetic medical image from the target medical image based on the altering.

It is to be understood that both the foregoing general description and the following detailed description are exemplary and explanatory only, and are not restrictive of the disclosed aspects, as claimed.

BRIEF DESCRIPTION OF THE DRAWINGS

The accompanying drawings, which are incorporated in and constitute a part of this specification, illustrate various exemplary aspects and together with the description, serve to explain the principles of the disclosed aspects.

FIG. 4A is a flowchart illustrating an exemplary method for training a machine learning system that is implemented in a style transfer-based synthetic image generation process, according to an exemplary aspect herein.

FIG. 6D is a flowchart illustrating an exemplary method for training a generative model implemented in a synthetic image generation process using simulated images and conditional generative methods, according to an exemplary aspect herein.

FIG. 7 is a flowchart illustrating an exemplary composition method for generating synthetic image data, according to an exemplary aspect disclosed herein.

DETAILED DESCRIPTION

Figure 1:
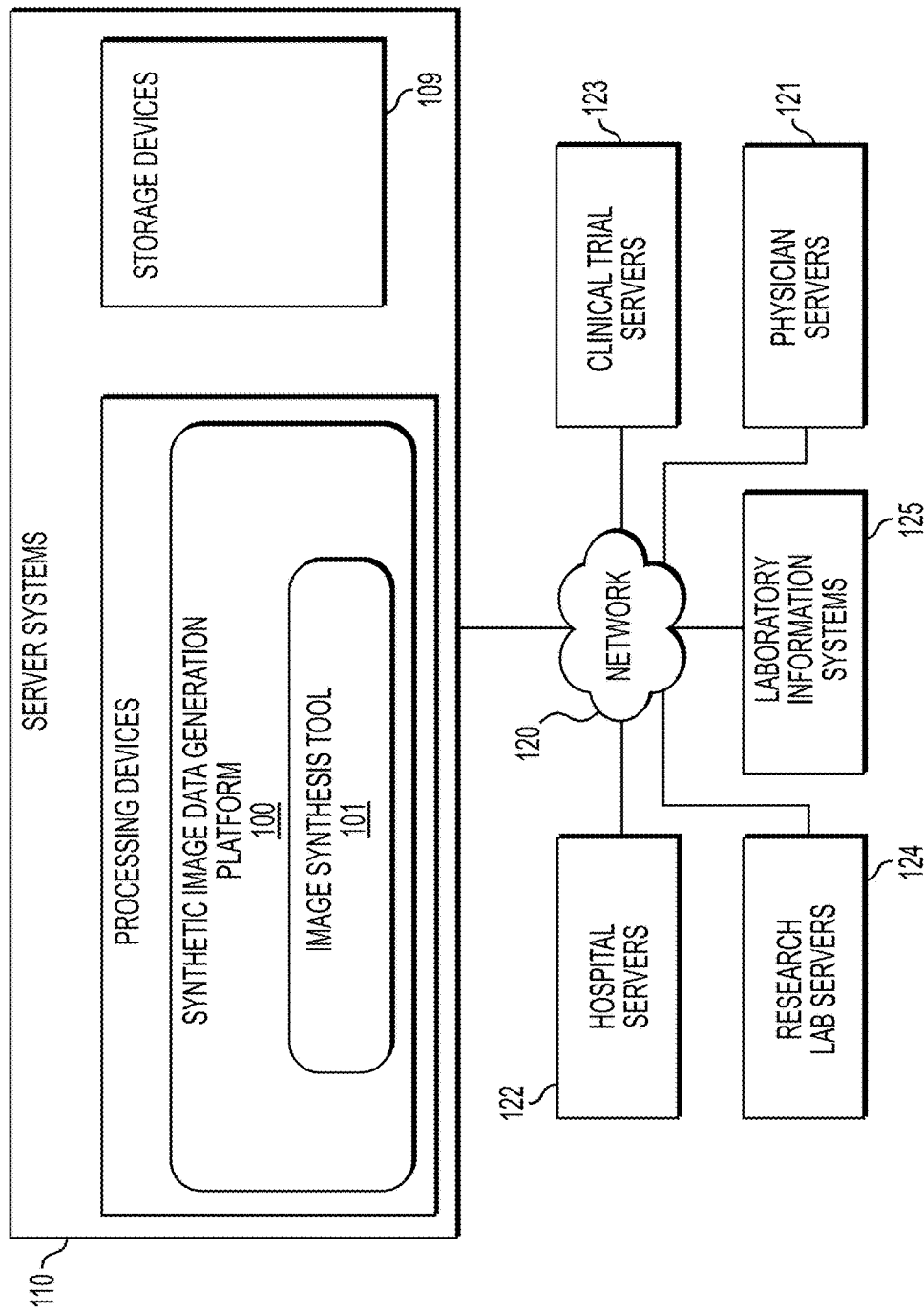
FIG. 1 illustrates an exemplary block diagram of a system and network for generating synthetic image data, according to techniques presented herein.

Reference will now be made in detail to the exemplary aspects of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Rare medical conditions, just like any other conditions, need to be diagnosed correctly, but often AI systems and medical professionals struggle to correctly diagnose rare presentations. One reason why rare conditions are hard to diagnose correctly is that rare conditions may not have large amounts of associated data and thus, AI systems and medical professionals have not seen enough presentations of these conditions to generalize the correct rules for diagnosis.

Existing approaches for solving this problem are inadequate. For example, from a machine learning side, oversampling, loss weighting, and/or similar approaches are used to enhance learning for rare data types. These, in general, do not work well because they do not create new variations. They are simply the same data that is "taught" to the AI system more frequently since they are of a rare type.

Techniques presented herein enable an increase in an amount of image data available for a rare condition or presentation thereof through a variety of methods, in order to improve training of machine learning systems and/or medical professionals. For example, plausible new forms of data (e.g., synthetic medical images) may be derived from existing medical image data containing a rare presentation so that an AI system and/or medical professional can be trained with more examples of the condition, which can increase diagnostic accuracy.

In machine learning, for example, there may be a relationship between increasing the amount of data for training and reducing error. Therefore, being able to generate realistic, synthetic image data may reduce the error of such systems.

The Environment

FIG. 1 illustrates a block diagram of a system and network for generating synthetic image data, according to an exemplary aspect of the present disclosure.

Specifically, FIG. 1 illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to electronic network 120, such as the Internet, through one or more computers, servers, and/or handheld mobile devices. According to an exemplary aspect of the present disclosure, electronic network 120 may also be connected to server systems 110, which may include processing devices that are configured to implement a synthetic image data generation platform 100, which includes an image synthesis tool 101 for synthesizing new medical image data from existing medical image data using one or more trained machine learning systems and/or through composition methods, according to exemplary aspects of the present disclosure. For example, image synthesis tool 101, as described below, refers to a process and system for deriving new, synthetic medical images from existing and/or simulated medical images using machine learning and/or composition methods.

Physician servers 121, hospital servers 122, clinical trial servers 123, research lab servers 124, and/or laboratory information systems 125 may create or otherwise obtain medical images of varying modalities. For example, digital pathology images, including one or more patients' cytology specimen(s), histopathology specimen(s), slide(s) of the cytology specimen(s), digitized images of the slide(s) of the histopathology specimen(s), or any combination thereof, may be created or obtained. Additionally or alternatively, images of other modality types, including magnetic resonance imaging (MRI), computed tomography (CT), X-ray, nuclear medicine imaging, or ultrasound, may be created or obtained. Physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. Physician servers 121, hospital servers 122, clinical trial servers 123, research lab servers 124, and/or laboratory information systems 125 may transmit medical images and/or patient-specific information to server systems 110 over electronic network 120 in a digital or electronic format.

Server systems 110 may include one or more storage devices 109 for storing medical images and data received from at least one of physician servers 121, hospital servers 122, clinical trial servers 123, research lab servers 124, and/or laboratory information systems 125. In some examples, storage devices 109 may include one or more data stores for storing the medical images. The one or more new, synthetic images that are derived by image synthesis tool 101 may also be stored within the one or more data stores. At least a portion of the medical images may include training images that are used for training AI systems and/or medical professionals to diagnosis conditions. In some examples, some of the training images may be withheld and used as testing images to evaluate an accuracy of a diagnostic system. Some of the medical images may present conditions (including the new, synthetic medical images derived), while others of the medical images may include reference images that do not include or present conditions. The medical images stored for use as training images may be stored in association with labels indicating data types of the medical images, including any conditions present, for use in training. Server systems 110 may also include processing devices for processing images and data stored in storage devices 109. Server systems 110 may further include one or more machine learning tool(s) or capabilities. For example, the processing devices may execute one or more machine learning systems utilized by image synthesis tool 101 of synthetic image data generation platform 100, according to one aspect. Alternatively or in addition, the present disclosure (or portions of the system and methods of the present disclosure) may be performed on a local processing device (e.g., a laptop).

Physician servers 121, hospital servers 122, clinical trial servers 123, research lab servers 124, and/or laboratory information systems 125 refer to systems used for viewing medical images of varying modalities, including digitized pathology slides. Medical images may be utilized by both medical professionals (e.g., pathologists, physicians, etc.) and AI systems alike for training purposes to improve accuracy in diagnosing conditions, among other tasks. A greater availability of image data presenting a particular condition or disease enhances both medical professionals and AI systems ability to learn given the increased variability in the presentation among the image data. However, rare conditions or diseases often do not have large amounts of associated image data, which necessarily limits an amount of variability that can be learned. For example, diagnosis of a rare condition or disease may be made difficult due to the presence of other conditions in conjunction with the rare condition or disease and/or treatment effects obscuring a typical presentation of the rare condition or disease (e.g., a variability not captured in a significant amount of image data used for learning).

According to an exemplary aspect of the present disclosure, synthetic image data generation platform 100 is implemented to generate new, synthetic medical images from existing medical image data containing a rare presentation using one or more machine learning systems and/or composition methods to increase an amount of medical image data associated with the rare presentation that is available for training of machine learning systems and/or medical professionals.

In some aspects, image synthesis tool 101 of synthetic image data generation platform 100 may include a training image platform and/or a target image platform. The training image platform, according to one aspect, may create or receive training images that are used to train one or more machine learning systems for providing various outputs for generating synthetic medical images. Exemplary machine learning systems are discussed in detail below. In some examples, the synthetic medical images may be a direct output of one or more of the machine learning systems. In other examples, the output of one or more of the machine learning systems may be used as input to further processes that enable generation of the synthetic medical images. The training images may be received from any one or any combination of server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics simulators, graphics rendering engines, 3D models, etc.). In other examples, a third party may train one or more of the machine learning systems and provide the trained machine learning system(s) to server systems 110 for storage (e.g., in storage devices 109) and execution by synthetic image data generation platform 100. The target image platform, according to one aspect, may receive a request for a medical image having a specific data type and execute one or more of the machine learning systems trained by the training image platform to generate a synthetic medical image of the specific data type requested. For example, the request may be received from any one or any combination of the server systems 110, physician servers 121, hospital servers 122, clinical trial servers 123, research lab servers 124, and/or laboratory information systems 125. In another example, the request may be automatically be generated by synthetic image data generation platform 100 in response to detecting a number of medical images stored in storage devices 109 (e.g., a number of training images) having the specific data type is below a predefined threshold.

Generating Synthetic Image Data

Figure 2:
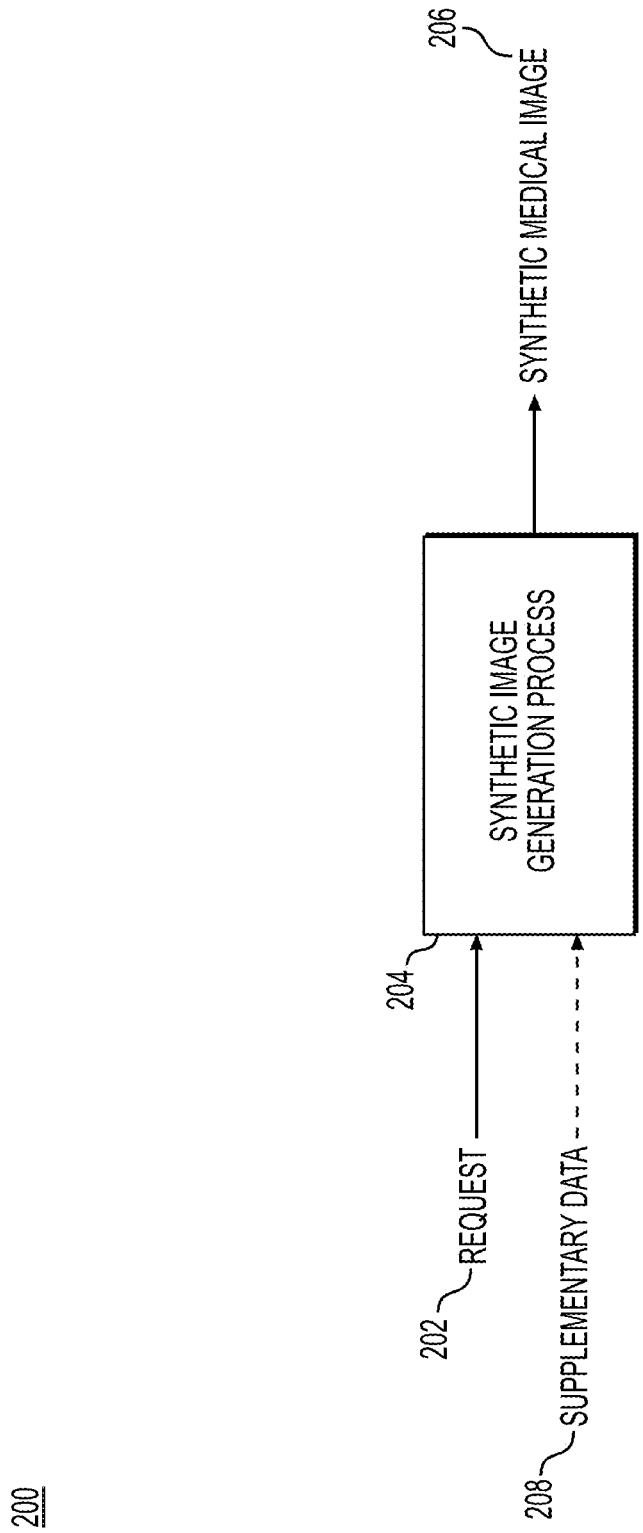
FIG. 2 is a block diagram illustrating a generation process for a synthetic image, according to one or more exemplary aspects disclosed herein.

FIG. 2 is a block diagram 200 illustrating a generation process for a synthetic image, according to one or more exemplary aspects disclosed herein. The generation process may be performed by image synthesis tool 101 of synthetic image data generation platform 100 automatically and/or in response to a request from a user (e.g., physician, pathologist, administrator, etc.).

A request 202 for a medical image of a specific data type may be provided as input to a synthetic image generation process 204. In some examples, the request 202 may be automatically generated in response to detecting that a number of available medical images having the specific data type (e.g., stored in storage devices 109) is below a predefined threshold. In other examples, the request 202 may be input by the user. The specific data type requested may include an image modality (e.g., digital pathology, magnetic resonance imaging (MRI), computed tomography (CT), X-ray, nuclear medicine imaging, or ultrasound), a target anatomical region, a target morphology, a presence or absence of a condition, and/or or a presence or absence of a treatment effect. In some examples, the data type includes at least a presence of a rare condition or disease for which a large amount of medical image data is not available. As one specific, non-limiting example, the requested data type may be a pathology slide for breast tissue with rare, mucinous cancer that occurs in less than 5% of cancers. A condition may be determined to be rare if it is associated with an occurrence rate below a predetermined threshold.

The synthetic image generation process 204 may execute one or more trained machine learning systems or utilize composition-based methods to generate a synthetic medical image 206 in a digital or electronic format having the specific data type requested for provision as output. An example synthetic image generation process 204 may include a machine-learning based process, such as a style-transfer based method, a conditional generative method, or a combined simulated image and conditional generative method, and/or a composition-based method, each described in detail below.

Optionally, in some examples, supplementary data 208 may also be provided as input to the synthetic image generation process 204. Supplementary data 208 may include a reference medical image, for example, that may be used to further facilitate the generation of the synthetic medical image 206. For example, supplementary data 208 may be used for the content thereof (e.g., may be a target medical image) or may be used to enhance a realistic appearance of the synthetic medical image 206 dependent on the particular synthetic image generation process 204 utilized. In some examples, supplementary data 208 may be stored in the one or more data stores (e.g., in storage devices 109) upon receipt.

Figure 3:
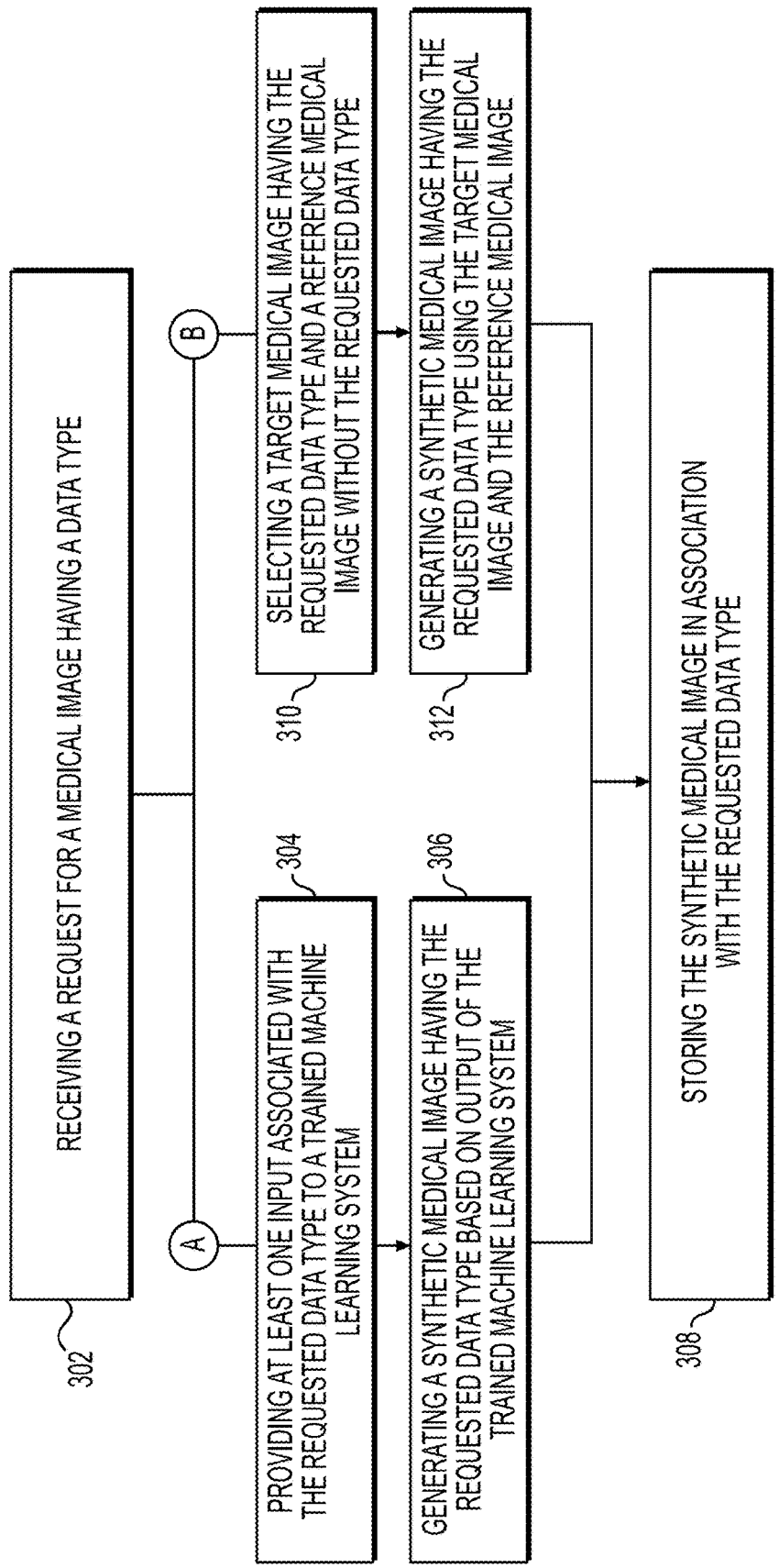
FIG. 3 is a flowchart illustrating exemplary methods for generating a synthetic image, according to one or more exemplary aspects disclosed herein.

FIG. 3 is a flowchart illustrating an exemplary method 300 for generating a synthetic medical image, according to one or more exemplary aspects disclosed herein. The exemplary method 300 illustrates how to derive synthetic medical images presenting rare conditions or diseases for subsequent use in training machine learning models, training medical professionals, and/or evaluating performance or accuracy of medical diagnostic systems. There may be a number of ways to derive the synthetic medical image. Several derivation methods using trained machine learning systems and/or composition-based methods are described herein; however, this list is not exhaustive, and other approaches may be implemented.

Exemplary method 300 (e.g., steps 302-312) may be performed by image synthesis tool 101 of synthetic image data generation platform 100 automatically and/or in response to a request from a user (e.g., pathologist, patient, oncologist, technician, administrator, etc.). Exemplary method 300 may include one or more of the following steps.

In step 302, method 300 may include receiving a request (e.g., request 202) for a medical image having a data type. In some examples, the request may be automatically generated in response to detecting that a number of available medical images having the specific data type (e.g., stored in storage devices 109) is below a predefined threshold. In other examples, the request may be input by the user. The specific data type requested may include an image modality (e.g., digital pathology, magnetic resonance imaging (MRI), computed tomography (CT), X-ray, nuclear medicine imaging, or ultrasound), a target anatomical region, a target morphology, a presence or absence of a condition, and/or or a presence or absence of a treatment effect. In some examples, the data type includes at least a presence of a rare condition or disease for which a large amount of image data is not available.

In some examples, after the request is received in step 302, method 300 may proceed to step 304 as shown by path A in FIG. 3. Path A provides example steps for generating a synthetic medial image via a machine learning-based generation process. In step 304, method 300 may include providing at least one input associated with (or indicative of) the requested data type to a trained machine learning system. Depending on a type of trained machine learning system used, a format of the input associated with the requested data type and any further input (e.g., supplementary data 208) may vary, as illustrated in FIGS. 4A-6F below describing three example machine learning systems. In step 306, method 300 may include generating a synthetic medical image having the requested data type (e.g., synthetic medical image 206) based on output of the trained machine learning system. In some examples, the synthetic medical image may be the direct output of the trained machine learning system. In other examples, output of the trained machine learning system may be used as input in further processes to generate the synthetic medical image.

Once the synthetic medical image having the request data type is generated, in step 308 of method 300, the synthetic medical image may be stored in a data store (e.g., in one of storage devices 109). In some examples, the synthetic medical image may be stored in association with the data type so that the synthetic medical image may be retrieved for use as a training image for a medical professional or AI system and/or a testing image for a medical diagnostic system, the data type being provided as a corresponding label for the training image. That is, the synthetic medical image and the corresponding label may be provided as a training dataset.

In other examples, after the request is received in step 302, method 300 may additionally or alternatively proceed to step 310 as shown by path B in FIG. 3. Path B provides example steps for generating a synthetic medial image via a composition-based generation process. In step 310, method 300 may include selecting a target medical image having the requested data type and a reference medical image without the requested data type. The target and reference medical images may be selected from the medical images stored in the one or more data stores (e.g., in storage devices 109). In step 312, method 300 may include generating a synthetic medical image having the requested data type (e.g. synthetic medical image 206) using the target medical image and the reference medical image, as described in more detail with reference to FIG. 7. Similar to path A, once the synthetic medical image having the requested data type is generated, in step 308 of method 300, the synthetic medical image may be stored in the data store.

Exemplary Machine Learning Technique: Using Style Transfer

Style transfer methods may use machine learning to impose a visual style on an image that the image did not originally have. For example, using style transfer for computational pathology, a style (e.g., local features) may be taken from a source medical image and imposed on another, target medical image. Style transfer may also enable content (e.g., global features) to be adjusted on an image. As a result, anticipated treatment effects such as global feature changes in tissue morphology may be introduced to a generated synthetic image in accordance with a treatment given to a patient having a rare condition.

Global features of a medical image may be associated with an entirety of (or at least areas of interest of) an image. In some aspects, the medical image may be a digital pathology image. Example global features for digital pathology images may include, but are not limited to, features resulting from a lab-specific preparation of a slide-mounted tissue specimen, a staining type used in the preparation (e.g., hematoxylin and eosin, hematoxylin, eosin, immunohistochemistry staining, etc.), and/or a type (e.g., make and model) of scanner used to scan slides to generate the images. Additional example global features may include, but are not limited to, features resulting from an age or diet of the patient (e.g., as seen in morphological features in the tissue specimen), particular conditions of the patient that affect a target organ (e.g., diabetes, cirrhosis, hepatitis, tuberculosis, genetic abnormalities, COVID-19, etc.), and/or patient-based geographic or racial population differences (e.g., skin color in skin biopsies).

Local features of a medical image that may be imposed on other medical image(s) via style transfer may be associated with a particular one or more areas within the image (e.g., a feature of a portion of a tissue specimen in a digital pathology image). Example local features include, but are not limited to, an effect of a treatment for a condition (e.g., treatment effects of chemotherapy, radiation, targeted hormonal treatments, etc., for various cancers), atrophy, specific types of lesions, and benign mimickers of a condition such as cancer. Additional example local features include, but are not limited to, tumor types or glands having a unique morphology, nerves and other normal morphologies that are mixed or arranged with uncommon morphologies (e.g., specific tumors or treatment effects), and tumors with specific genetic profiles and/or markers that affect morphology (e.g., Cadherin 1 (CDH1), human epidermal growth factor receptor 2 (Her2), estrogen receptor (ER) marker, progesterone receptor (PR) marker, etc.). Further example local features for digital pathology images include, but are not limited to, scanning artifacts and lab preparation artifacts (e.g., folds, over stained areas, dry areas, dust/dirt, bubbles, etc.).

Style transfer may include utilizing a trained machine learning system to take in two images, a source medical image and a target medical image in a digital or electronic format, and to impose the style of the source medical image onto the target medical image to generate a synthetic medical image, such that the internal statistical representations of the target medical image match the source medical image within the synthetic medical image. The steps for training and using a machine learning system to implement a style transfer approach for generating synthetic medical images are described below.

FIG. 4A is a flowchart illustrating an exemplary method 400 for training a machine learning system that is implemented in a style transfer-based synthetic image generation process, according to an exemplary aspect herein. Exemplary method 400 (e.g., steps 402-406) may be performed by a training image platform of image synthesis tool 101. Alternatively, method 400 may be performed by a third party system that provides the trained machine learning system to server systems 110 for storage (e.g., in storage devices 109) and execution by image synthesis tool 101. The trained machine learning system may be an image classification network. In some examples, the image classification network may be a multi-layer convolutional neural network (CNN) including, but not limited to, a VGG-19 model (e.g., a 19 layer deep CNN), a ResNet-50 model (e.g., a 50 layer deep CNN), or a U-Net model (e.g., a CNN developed for biomedical image segmentation), among other similar models.

According to one or more aspects, method 400 may include one or more of the following steps. In step 402, method 400 may include receiving, as training data, a plurality of medical images and corresponding labels. The medical images may be received in a digital or electronic format. The corresponding labels may identify global features and local features of the medical images. The training data may be stored in one or more data stores in storage devices 109, for example.

In step 404, method 400 may include training an image classification network using the training data to predict global features and local features of a medical image. For example, the image classification network may be trained to discriminate one or more regions within an image of a desired tissue type (digital pathology slides, MRIs, etc.). To perform the discrimination task, the network may learn two types of features in the image. A first feature type may include global features (e.g., high-level features) applicable to or effecting an entirety of the image or at least area of interest in the image, such as areas of tissue as opposed to organs or background. Global features may form or be associated with content of an image. A second feature type may include local features (e.g., low-level features) such as specific textures, local arrangements, or repeating patterns in one or more particular areas of tissue. Local features may form or be associated with style(s) of an image. Exemplary global and local features specific to a medical image are discussed in detail above.

In some examples, to enable learning, a training image may be provided as input to the image classification network. The image classification network may then output predicted global and local features of the training image. The predicted global and local features may be compared to the label corresponding to the training image (e.g., known local and global features of the training image) to determine a loss or error. The image classification network may be modified or altered (e.g., weights and/or bias in one or more layers of the network may be adjusted) based on the error to improve an accuracy of the image classification network. This process may be repeated for each training image or at least until a determined loss or error is below a predefined threshold. In some examples, some of the training images may with withheld and used to further validate or test the image classification network.

Additionally, as part of the training, layers of the image classification network having learned a feature may be identified and separated into two sets of layers. A first set of one or more layers may have learned global features and a second set of one or more layers may have learned local features.

In step 406, method 400 may include storing the trained image classification network in storage devices 109, for example. The trained image classification network may be subsequently retrieved for deployment by image synthesis tool 101 of synthetic image data generation platform 100 described below with reference to FIG. 4B.

Figure 4B:
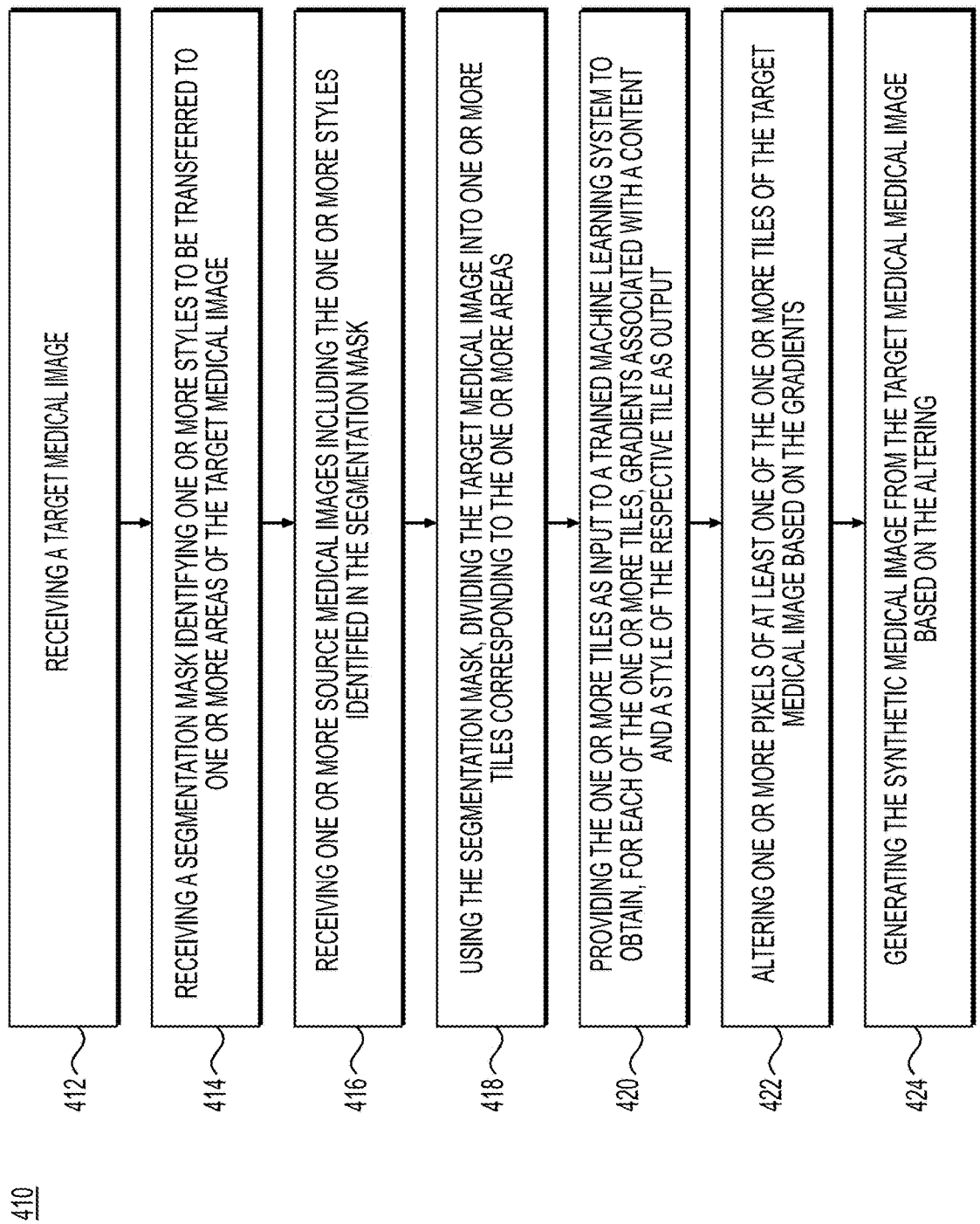
FIG. 4B is a flowchart illustrating an exemplary method for generating a synthetic image using a trained machine learning system in a style transfer-based synthetic image generation process, according to an exemplary aspect herein.

FIG. 4B is a flowchart illustrating an exemplary method 410 for generating a synthetic medical image using a trained machine learning system in a style transfer-based generation process, according to an exemplary aspect herein. Exemplary method 410 may be performed by a target image platform of image synthesis tool 101. The trained machine learning system may be the image classification network trained in accordance with method 400 described above with reference to FIG. 4A.

According to one or more aspects, method 410 may include one or more of the following steps. In step 412, method 410 may include receiving a target medical image. In some examples, the target medical image may be a reference medical image received as supplementary data (e.g., supplementary data 208). The target medical image may not have a data type desired. Rather, the target medical image may be an image that one or more styles of one or more sources images having the data type are transferred to as part of method 410.

In step 414, method 410 may include receiving a segmentation mask identifying one or more styles to be transferred to one or more areas of the target medical image. The segmentation mask may align with the target medical image, and the style(s) may be associated with a requested data type. For example, the segmentation mask may be included as part of a request (e.g., request 202) for a medical image having a data type, where the style(s) correspond to at least a portion of the requested data type. The requested data type may include an image modality, a target anatomical region, a target morphology, a presence or absence of a condition, and/or a presence or absence of a treatment effect.

In step 416, method 410 may include receiving one or more source medical images including the style(s) identified in the segmentation mask (e.g., the styles to be transferred to the target medical image). In some examples, the source medical images may also be included as part of the request (e.g., request 202).

In step 418, method 410 may include dividing the target medical image into one or more tiles corresponding to the one or more areas using the segmentation mask. For example, the target medical image may include a plurality of tiles, and if the segmentation mask includes a first style for a first image area and a second style for a second image area, the target medical image may be divided into at least a first portion of tiles from the plurality of tiles that correspond to the first image area and a second portion of tiles from the plurality of tiles that correspond to the second image area.

In step 420, method 410 may include providing the one or more tiles as input to a trained machine learning system, such as the trained image classification network described with reference to FIG. 4A, to obtain, for each of the one or more tiles, gradients (e.g., embeddings) associated with a content and a style of the respective tile as output. In some examples, the gradients may be a representation (e.g., a numerical representation) for the respective tile of the target medical image that encodes features of the respective tile. For example, the trained image classification network may predict global features associated with content of a given tile utilizing the first set of one or more layers identified during training of the image classification network to encode global features or content information for the given tile in a first gradient (e.g., a first embedding). Additionally, the trained image classification network may predict local features associated with style of a given tile utilizing the second set of one or more layers identified during training of the image classification network to encode local features or style information for the given tile in a second gradient (e.g., a second embedding).

In step 422, method 410 may include altering one or more pixels of at least one of the one or more tiles of the target medical image based on the gradients. For example, the pixel(s) in a given tile may be altered to generate an altered tile (e.g., a new tile to be used to generate a synthetic image). In some aspects, a particular representation for each of the one or more of the features within the respective gradients of the given tile may be identified (e.g., as elements of the gradients). The given tile may be altered by removing and/or replacing one or more of the representations with (e.g., by copying over) one or more desired feature representations from other images, such as the one or more source medical images, in a transfer process. The other images may have also been input to the trained machine learning system to receive respective gradients representing the content and styles thereof and identify a representation of the features within the gradients for storage and subsequent use in the transfer process.

Specific to this example, the pixel(s) in a given tile may be altered to generate an altered tile that maintains the content of the target medical image while transferring the one or more styles of the one or more source medical images to the target medical image (e.g., by copying representations of at least one or more local features of the source medical image(s) to the target medical image). To achieve this, a first similarity metric measuring a similarity in content between the target medical image and the synthetic medical image may be computed and alterations may be performed to maximize the first similarity metric. Similarly, a second similarity metric measuring a similarity in style between the synthetic medical image and the one or more source medical images may be computed and alterations may be performed to maximize the second similarity metric. According to some aspects, step 422 may be an iterative altering process where a next one or more pixels of a given tile are altered in a same or similar manner described above. As one non-limiting example, the altering process may continue until a change in the first similarity metric and/or the second similarity metric from a previous alteration to a current alteration stops increasing.

In step 424, method 410 may include generating a synthetic medical image based on the altering in step 422. For example, a corresponding tile in the target medical image may be replaced with the at least one of the one or more tiles of the target medical image having the one or more pixels altered in step 422 to generate the synthetic medical image (e.g., synthetic medical image 206). In some examples, one or more image processing techniques may be implemented following the tile replacement(s) to smooth over any seams that may be present between one or more tiles or groupings of tiles in the synthetic medical image. Example image processing techniques may include an N×N convolution or Gaussian smoothing, among other similar techniques. The synthetic medical image may then be stored in one or more data stores (e.g., in storage devices 109) for subsequent use in training or performance evaluation, for example.

Imposing Treatment Effects from Endocrine Therapy in Prostate Cancer Using Style Transfer Methods In many forms of cancer treatment, the morphology of the tissue changes for both benign and cancerous tissue. For example, endocrine therapy in prostate cancer shrinks both benign and cancerous cells in the prostate, making them look unusual in medical images (e.g., in digital pathology slides). The aspects disclosed herein can be used to generate synthetic medical images with treatment effects by taking as input a target medical image without treatment effects, along with a segmentation mask and one or more source images having one or more treatment effects desired to be included utilizing the above-described style transfer-based synthetic image generation process (e.g., by transferring the style of the source images to the target image to yield the synthetic medical image).

Exemplary Machine Learning Technique: Generating Synthetic Images Using Conditional Generative Methods Conditional generative methods may include training and use of a machine learning system to generate a synthetic image from a semantic segmentation annotation.

Figure 5A:
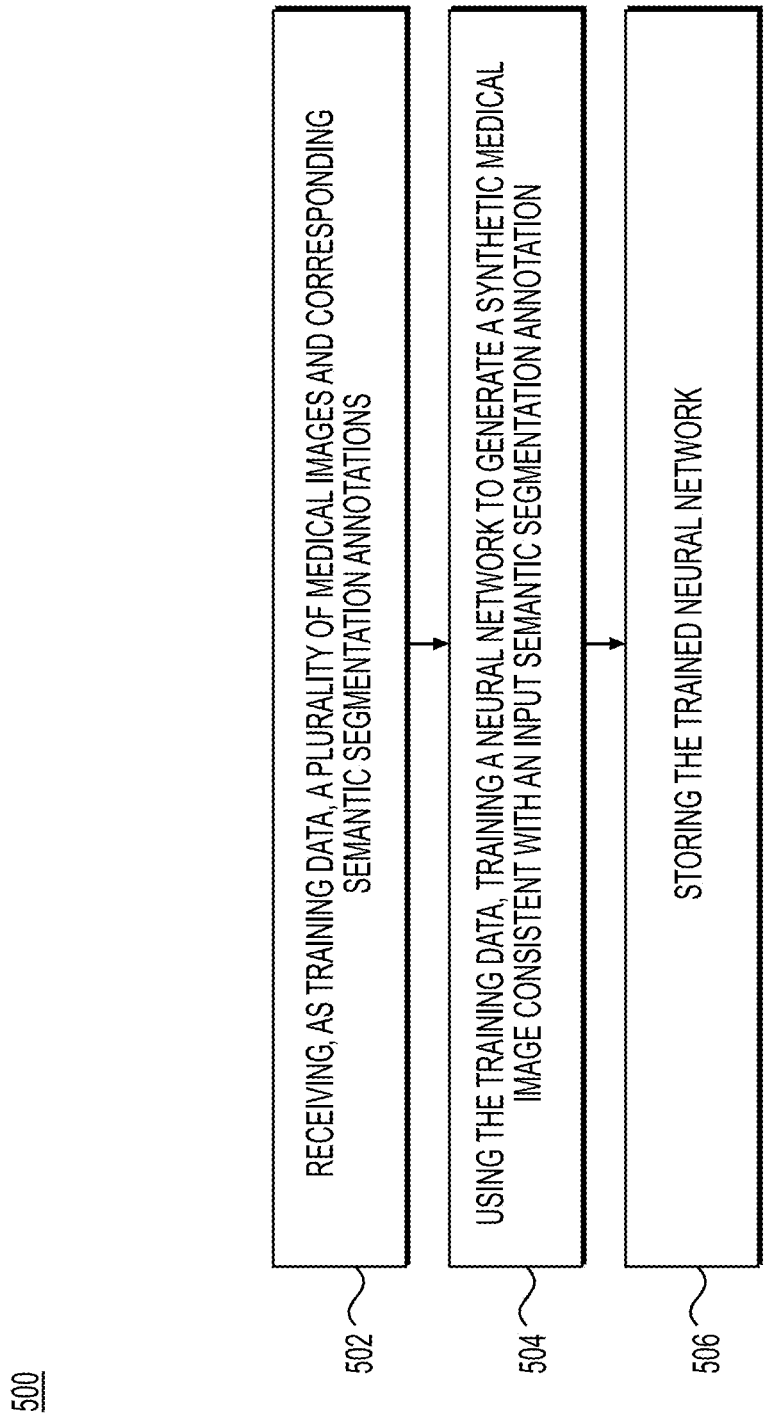
FIG. 5A is a flowchart illustrating an exemplary method for training a machine learning system that is implemented in a synthetic image generation process using conditional generative methods, according to an exemplary aspect herein.

FIG. 5A is a flowchart illustrating an exemplary method 500 for training a machine learning system that is implemented in a synthetic image generation process using conditional generative methods. Exemplary method 500 (e.g., steps 502-506) may be performed by a training image platform of image synthesis tool 101. Alternatively, method 500 may be performed by a third party system that provides the trained machine learning system to server systems 110 for storage (e.g., in storage devices 109) and execution by image synthesis tool 101. The trained machine learning system may be a neural network. In some examples, the neural network may be a deep neural network having a plurality of hidden layers to enable learning of more complex patterns.

In step 502, method 500 may include receiving, as training data, a plurality of medical images and corresponding semantic segmentation annotations for the medical images. At least a portion of the training data may include medical images presenting rare conditions or morphologies, while one or more other portions of the training data may include medical images presenting common (e.g., non-rare) conditions or morphologies. In some examples, the training data may be medical images received in a digital or electronic format from physician servers 121, hospital servers 122, clinical trial servers 123, research lab servers 124, and/or laboratory information systems 125 over electronic network 120 and stored in one or more data stores in storage devices 109.

In step 504, method 500 may include training a machine learning system, such as a neural network, to generate, as output, a synthetic medical image consistent with an input semantic segmentation annotation. In one non-limiting example, the neural network may be trained using a spatially-adaptive normalization method, as described below with reference to FIG. 5B.

In step 506, method 500 may include storing the trained neural network in storage devices 109, for example. The trained neural network may be subsequently retrieved for deployment by image synthesis tool 101 of synthetic image data generation platform 100 described below with reference to FIG. 5C.

Figure 5B:
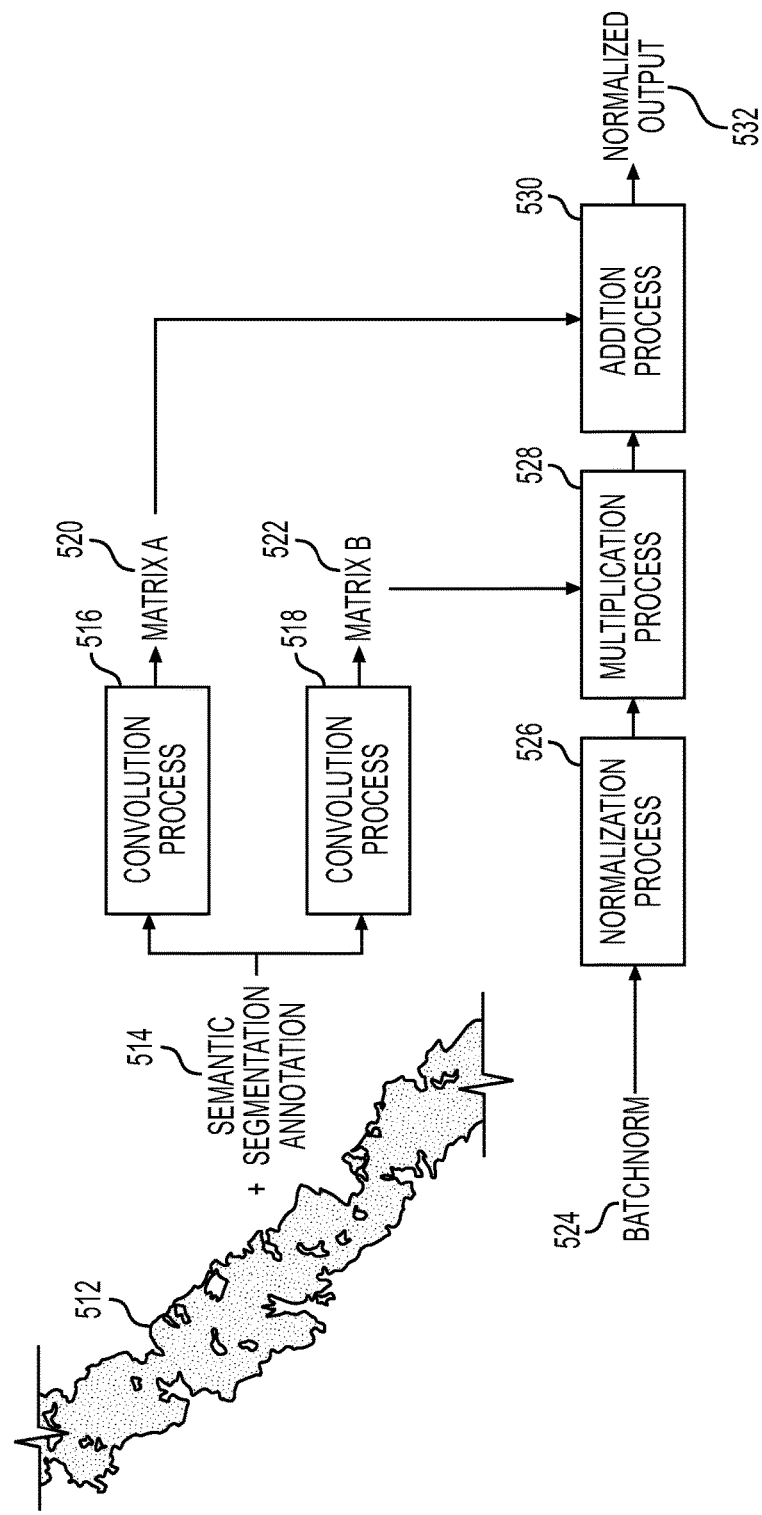
FIG. 5B is a conceptual diagram illustrating a spatially-adaptive normalization (SPADE) method for training a machine learning system that is implemented in a synthetic image generation process using conditional generative methods, according to an exemplary aspect herein.

FIG. 5B is a conceptual diagram illustrating a spatially-adaptive normalization method (SPADE) 510 for training a machine learning system, such as the neural network described with reference to FIG. 5A, that is implemented in a synthetic image generation process using conditional generative methods. A neural network may include a series of layers termed "neurons" or "nodes." A neural network may comprise an input layer, to which data is presented, one or more internal layers, and an output layer. The internal layers may include convolutional layers, pooling layers, or normalization layers. In some examples, the internal layers may be hidden layers. The number of neurons in each layer may be related to the complexity of a problem to be solved. Input neurons may receive data being presented and then transmit the data to the first internal layer through the connections' weight. For example, each neuron in the input layer may be connected to every other neuron in the first internal layer, each neuron in the first internal layer may be similarly connected to every other neuron in a next layer (e.g., a next internal layer or the output layer), and so on. Each connection between two nodes may have an associated weight.

Using SPADE, a training medical image 512 and a corresponding semantic segmentation annotation 514 for the training medical image 512 may be received as input. The semantic segmentation annotation 514 may be projected onto an embedding space of the neural network (e.g., onto an input layer) and then convolved 516, 518 through convolutional layers to output two matrices, Matrix A 520 and Matrix B 522. In some examples, the semantic segmentation annotation 514 may first be converted to a semantic segmentation mask and the mask is projected onto the embedding space. A batch of data 524 may be normalized in normalization process 526, and multiplied by matrix B 522 in multiplication process 528. In summation process 530, Matrix A 520 may then be added to the resulting matrix from the multiplication process 528 (e.g., a transformed matrix B) to yield a normalized output 532. The normalized output 532 may be a synthetic medical image. In some examples, a loss or error may then be determined by comparing the synthetic medical image to the training medical image 512 (e.g., the real medical image) to which the semantic segmentation annotation 514 corresponds. The neural network may be modified or altered (e.g., weights in one or more layers of the network may be adjusted) based on the error to improve an accuracy of the neural network.

Figure 5C:
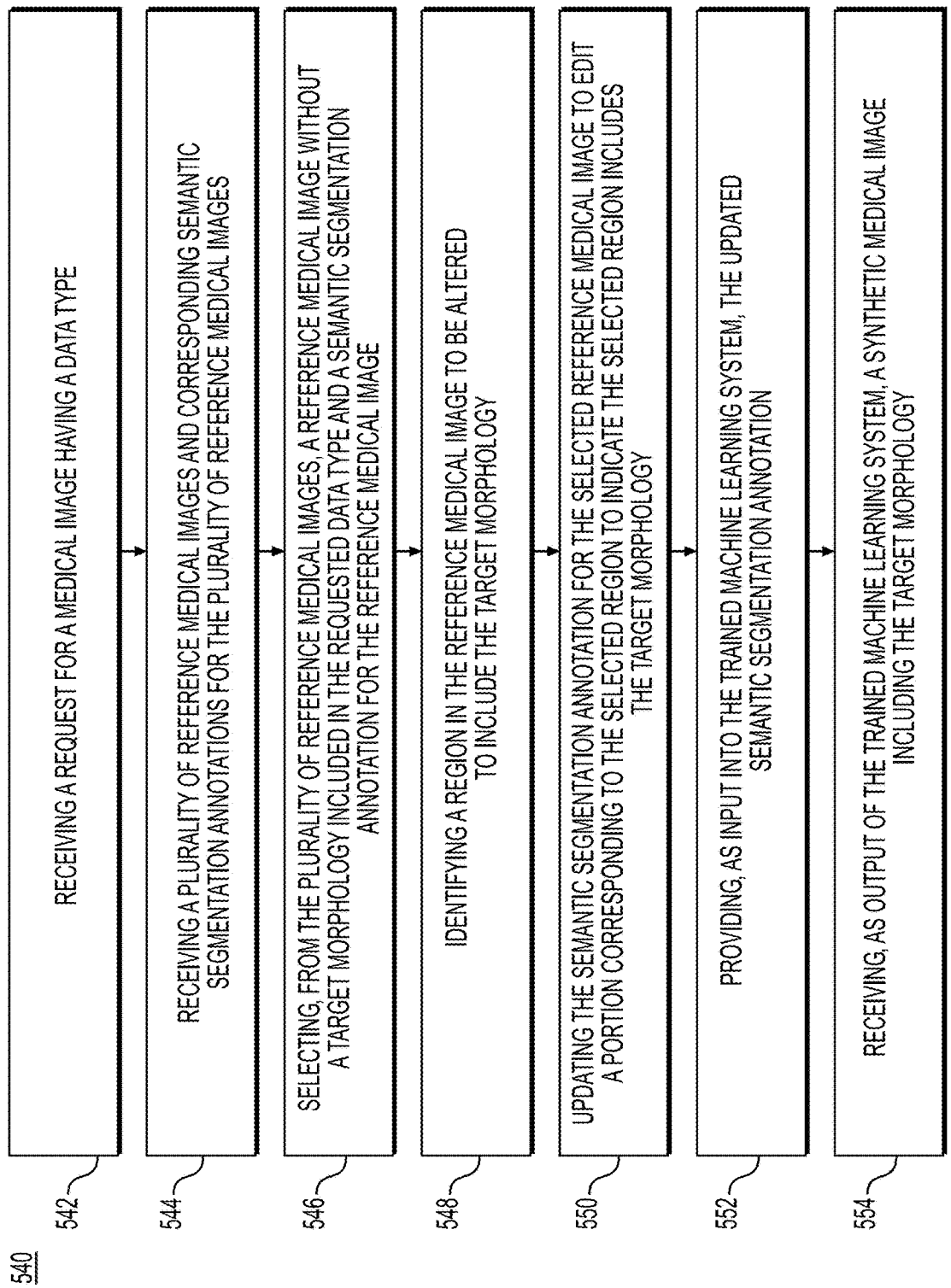
FIG. 5C is a flowchart illustrating an exemplary method for generating a synthetic image using a trained machine learning system in a synthetic image generation process based on conditional generative methods, according to an exemplary aspect herein.

FIG. 5C is a flowchart illustrating an exemplary method 540 for generating a synthetic medical image using a trained machine learning system in a conditional generative method-based generation process, according to an exemplary aspect herein. Exemplary method 540 (e.g., steps 542-554) may be performed by a target image platform of image synthesis tool 101. The trained machine learning system may be the neural network trained in accordance with method 500 described above with reference to FIG. 5A and/or FIG. 5B.

According to one or more aspects, method 540 may include one or more of the following steps. In step 542, method 540 may include receiving a request for a medical image having a data type (e.g., request 202). In this exemplary method 540, the data type may include at least a morphology of interest, hereinafter referred to as a target morphology. In step 544, method 540 may include receiving a plurality of reference medical images and corresponding semantic segmentation annotations for the reference medical images. The reference medical images and the corresponding semantic segmentation annotations may be examples of supplementary data that is received (e.g., supplementary data 208), and stored in one or data stores in storage devices 109.

In step 546, method 540 may include selecting, from the plurality of reference medical images, a reference medical image without the target morphology requested and a semantic segmentation annotation for the reference medical image. In step 548, method 540 may include identifying a region in the reference medical image to be altered to include the target morphology. For example, the identified region may include a current morphology that is to be altered to or replaced with the target morphology. In step 550, method 540 may include updating the semantic segmentation annotation for the reference medical image to edit a portion of the semantic segmentation annotation corresponding to the identified region to indicate the region includes the target morphology.

In step 552, method 540 may include may include providing the updated semantic segmentation annotation as input to a trained machine learning system, such as the trained neural network described above with reference to FIGS. 5A and/or 5B. In step 554, method 540 may include may include receiving a synthetic medical image as output of the trained machine learning system (e.g., synthetic medical image 206), where the synthetic medical image includes the target morphology. The synthetic medical image may then be stored in one or more data stores (e.g., in storage devices 109) for subsequent use in training or performance evaluation, for example.

Exemplary Machine Learning Technique: Generating Synthetic Medical Images Using Simulated Images and Conditional Generative Methods A graphics simulation system (also referred to herein as a graphics simulator) may generate mock or simulated or virtual images. Often, these simulated images may appear artificial and non-realistic, making such simulated images less useful for training purposes. However, by using one or more trained machine learning systems in conjunction with the graphics simulator, more realistic versions of the simulated images provided as input to the trained machine learning systems may be generated and provided as output.

FIGS. 6A through 6G below describe an example system including a graphics simulator and at least two machine learning systems, including the training and use thereof, that are used in conjunction with the graphics simulator to enable generation of synthetic medical images suitable for training and evaluation purposes.

Figure 6A:
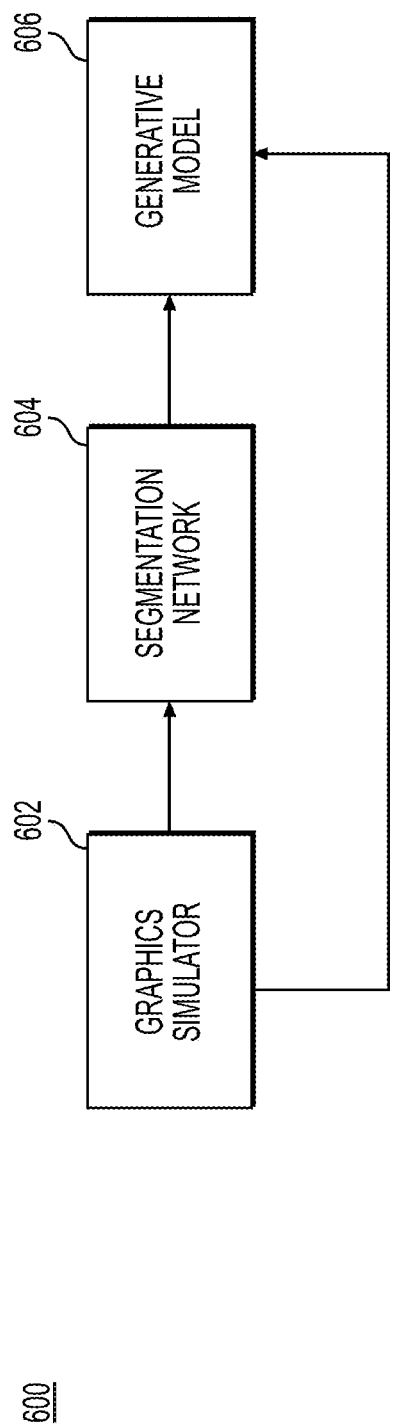
FIG. 6A is a block diagram illustrating an example system for generating synthetic images using simulated images and conditional generative methods.

FIG. 6A is a block diagram illustrating an example system 600 for generating synthetic medical images using simulated images. System 600 may include a graphics simulator 602 and at least two machine learning systems: a segmentation network 604 and a generative model 606. In some examples, graphics simulator 602 may be built and executed by synthetic image data generation platform 100. In other examples, graphics simulator 602 may be provided by a third party. Simulated medical images generated by the graphics simulator 602 may be comprised of parameterized synthetic image data that is a high-level representation of real medical image data. As a result, the simulated medical image may be appear artificial or non-realistic. For example, the simulated medical image may comprise a cartoon version of the real medical image lacking most of the texture and realistic proportions, but conserving the general shape and location of elements or structures. Segmentation network 604 may be trained and used to predict parametrized synthetic image data that is output by graphics simulator 602. Generative model 606 may be trained (based on input from segmentation network 604) and used to augment parameterized synthetic image data received from graphics simulator 602 to approximate or predict real medical image data to which the parameterized synthetic data corresponds. The predicted real image data may be a more realistic version of the parameterized synthetic data that may then be provided as output of the generation process (e.g., output as synthetic medical image 206).

Figure 6B:
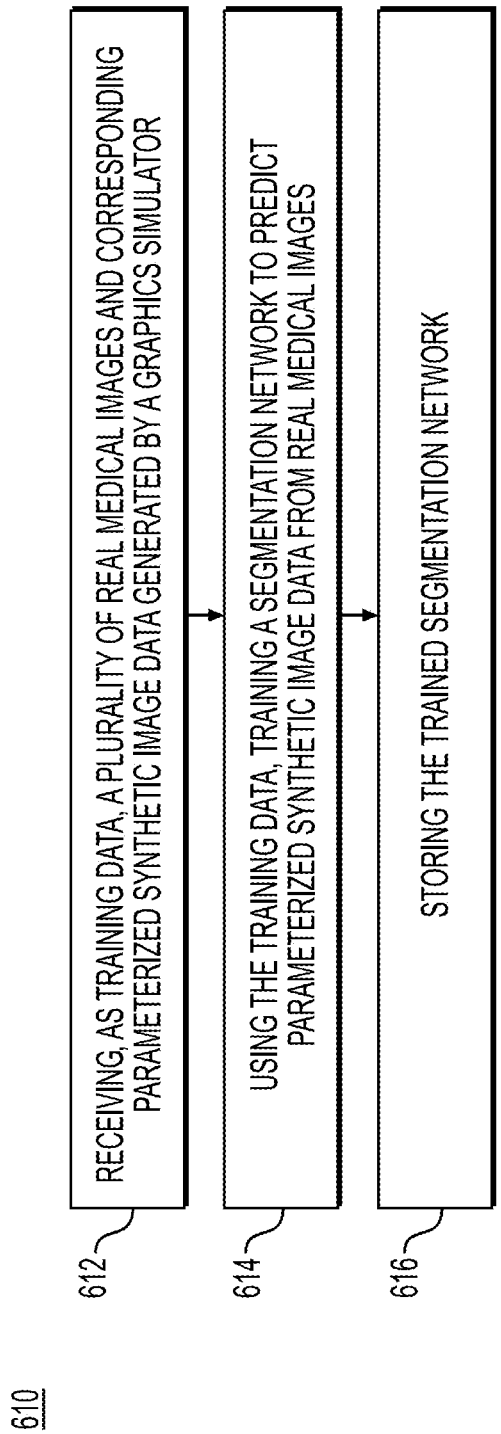
FIG. 6B is a flowchart illustrating an exemplary method for training a segmentation network implemented in a synthetic image generation process using simulated images and conditional generative methods, according to an exemplary aspect herein.

FIG. 6B is a flowchart illustrating an exemplary method 610 for training segmentation network 604. Exemplary method 610 (e.g., steps 612-616) may be performed by a training image platform of image synthesis tool 101. Alternatively, method 610 may be performed by a third party system that provides trained segmentation network 604 to server systems 110 for storage (e.g., in storage devices 109) and execution by image synthesis tool 101.

Exemplary method 610 may include the following steps. In step 612, method 610 may include receiving, as training data, a plurality of real medical images (e.g., training images) and corresponding parametrized synthetic image data generated by the graphics simulator 602 for the plurality of medical images (e.g., corresponding labels for the training images).

Figure 6C:
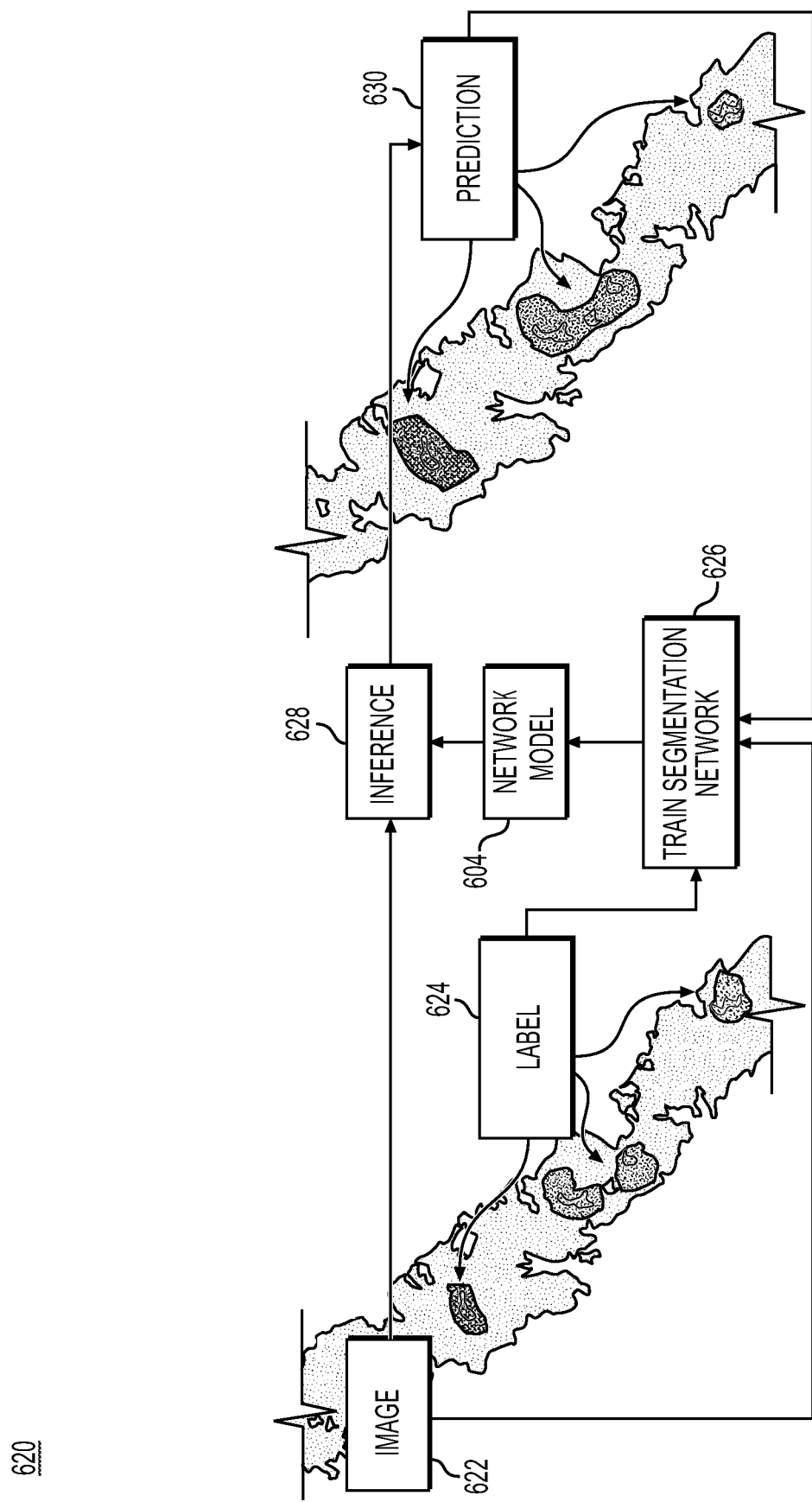
FIG. 6C is a conceptual diagram illustrating a training of a segmentation network, according to an exemplary aspect herein.

In step 614, method 610 may include training segmentation network 604 to predict parametrized synthetic image data from real medical images using the training data. FIG. 6C is a conceptual diagram 620 illustrating the training of the segmentation network 604. In some examples, to enable learning, a real medical image 622 (e.g., a training image) and a corresponding label 624 comprised of parametrized synthetic image data generated by the graphics simulator 602 for the real medical image 622 may be provided to build and train segmentation network 604 at step 626. In response to receiving the real medical image 622, segmentation network 604 may undergo an inference process at step 628 to output a prediction 630, the prediction 630 including predicted parametrized synthetic image data for the real medical image 622. The predicted parametrized synthetic image data may be compared to label 624 to determine a loss or error that is further used as part of the training of the segmentation network 604 at step 626. For example, segmentation network 604 may be modified or altered (e.g., weights and/or bias in one or more layers of the network may be adjusted) based on the error to improve an accuracy of segmentation network 604. This process may be repeated for each training image or at least until a determined loss or error is below a predefined threshold. In some examples, some of the training images may with withheld and used to further validate or test the image classification network.

Returning to FIG. 6B, in step 616, method 610 may include storing the trained segmentation network 604 in one or more data stores in storage devices 109, for example. The trained segmentation network 604 may be subsequently retrieved for training the generative model 606 as described in FIG. 6D below.

In the example described above, corresponding label 624 for real medical image 622 may be comprised of parametrized synthetic image data. In other examples, a segmentation for the real medial image 622 may be provided as a corresponding label to enable learning. The segmentation may be a mask for the pararmetrized synthetic image data comprising an array of the same shape but only containing categorical values for individual pixels of the image that encode what is meant to be present in the respective pixels.

FIG. 6D is a flowchart illustrating an exemplary method 640 for training generative model 606. Exemplary method 640 (e.g., steps 642-646) may be performed by a training image platform of image synthesis tool 101. Alternatively, method 640 may be performed by a third party system that provides trained generative model 606 network to server systems 110 for storage (e.g., in storage devices 109) and execution by image synthesis tool 101. Generative model 606 may be a U-Net model, a generative adversarial network (GAN), or a variational autoencoder (VAE), among other similar types of generative models.

Exemplary method 640 may include the following steps. In step 642, method 640 may include receiving, as training data, parameterized synthetic image data predicted for a plurality of medical images by trained segmentation network 604 described above with reference to FIGS. 6B and 6C. Additionally, the plurality of real medical images themselves (e.g., to which the predicted parameterized synthetic image data corresponds) may be received as labels.

Figure 6E:
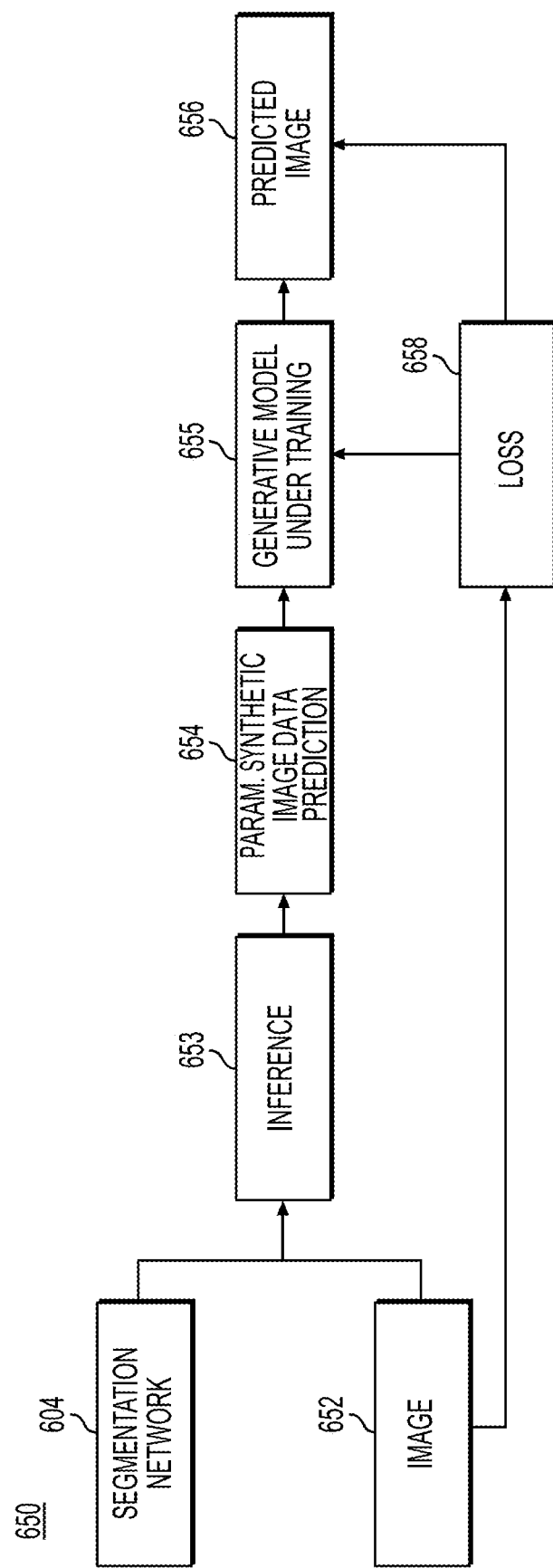
FIG. 6E is a conceptual diagram illustrating a training of a generative model, according to an exemplary aspect herein.

In step 644, method 640 may include training generative model 606 to predict or approximate a real medical image from parametrized synthetic image data received as input. FIG. 6E is a conceptual diagram 650 illustrating an exemplary process for performing the training of generative model 606 in step 644. Trained segmentation network 604 having received a real medical image 652 as input may output a prediction 654 as part of inference process 653. Prediction 654 may include predicted parametrized synthetic image data for real medical image 652 that is provided as training data input to generative model 606 as part of the training process in step 655. For example, generative model 606 may predict or approximate a real medical image corresponding to the predicted parametrized synthetic image data (e.g., predicted image 656). Predicted image 656 may be compared to the real medical image 652 to which the predicted parametrized synthetic image data actually corresponds (e.g., compared to the corresponding label also received as training data input) to determine a loss or error at step 658. Generative model 606 may be modified or altered (e.g., weights and/or bias in one or more layers of the network may be adjusted) based on the error to improve an accuracy of generative model 606. This process may be repeated for the segmentation predicted for each of the plurality of medical images by trained segmentation network 604 received as training data or at least until a determined loss or error is below a predefined threshold. In some examples, some of the training data may with withheld and used to further validate or test generative model 606.

Returning to FIG. 6D, in step 646, method 640 may include storing trained generative model 606 in one or more data stores in storage devices 109, for example. Trained generative model 606 may be subsequently retrieved for deployment by image synthesis tool 101 of synthetic image data generation platform 100 described below with reference to FIG. 6F.

Figure 6F:
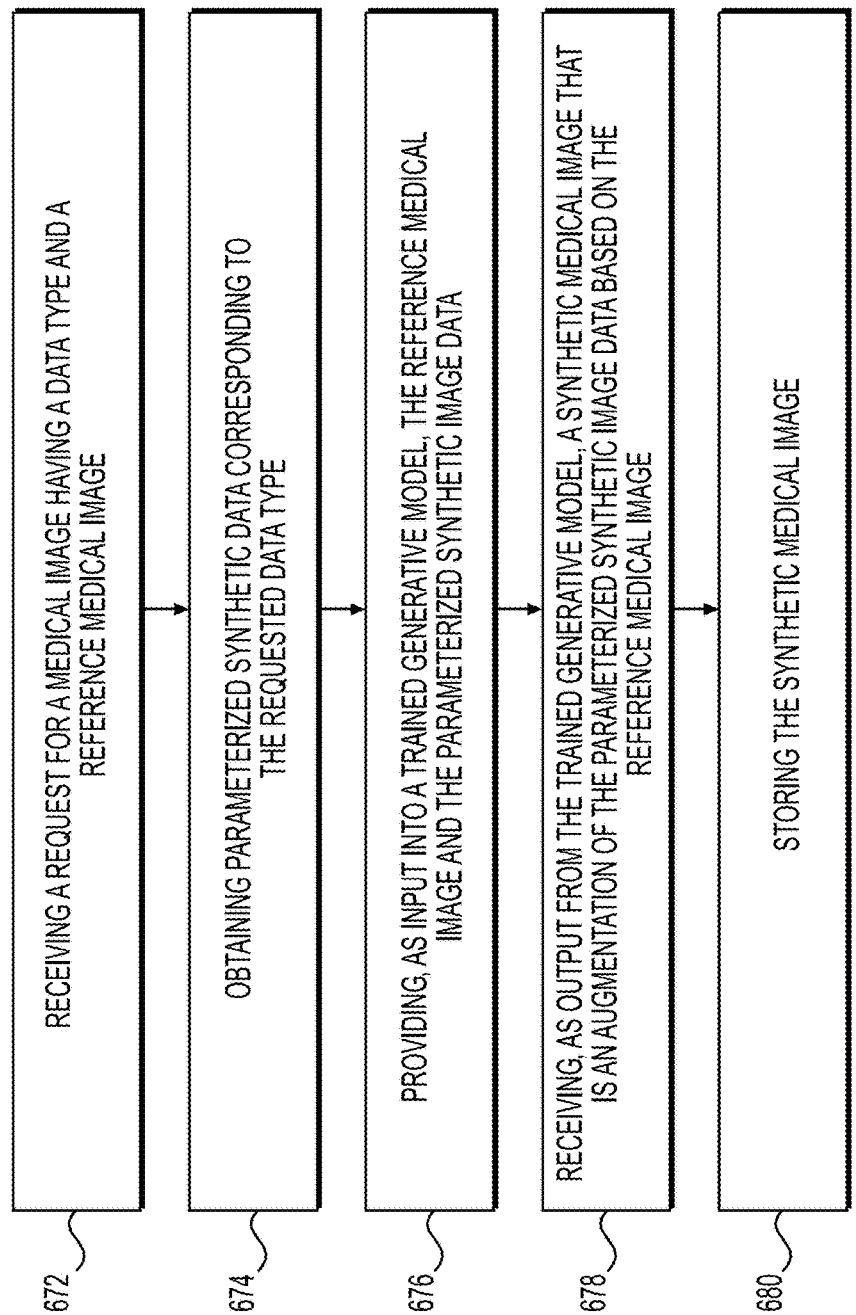
FIG. 6F is a flowchart illustrating an exemplary method for generating a synthetic image using a trained generative model based on a synthetic image generation process using simulated images and conditional generative methods, according to an exemplary aspect herein.
Figure 6G:
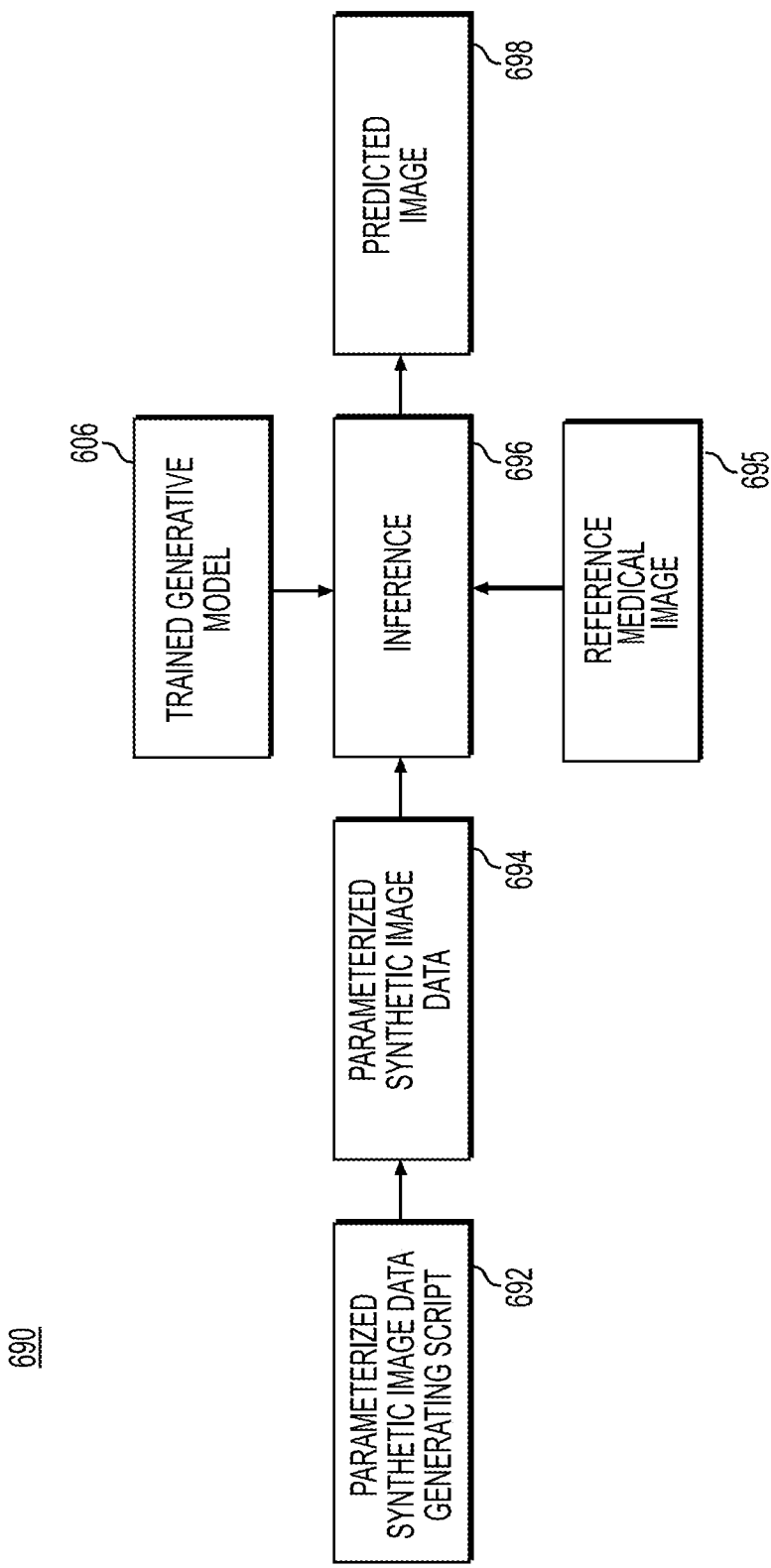
FIG. 6G is a conceptual diagram illustrating use of a trained generative model for generating a synthetic image, according to an exemplary aspect herein.

FIG. 6F is a flowchart illustrating an exemplary method 670 for generating a synthetic image using a trained machine learning model based on a synthetic image generation process using simulated images and conditional generative methods. Exemplary method 670 may be performed by a target image platform of image synthesis tool 101. The trained machine learning system may be generative model 606 trained in accordance with method 640 described above with reference to FIGS. 6D and 6E.

According to one or more aspects, method 670 may include one or more of the following steps. In step 672, method 670 may include receiving a request for a medical image having a data type (e.g., request 202) along with a reference medical image (e.g., as part of supplementary data 208). In step 674, method 670 may include obtaining parametrized synthetic image data corresponding to the requested data type. For example, graphics simulator 602 may generate the parameterized synthetic image data (e.g., generate a simulated image) from a medical image having the requested data type.

In step 676, method 670 may include providing the reference medical image and the parametrized synthetic image data as input to a trained machine learning system, such as trained generative model 606. In step 678, method 670 may include receiving, as output from trained generative model 606, a synthetic medical image (e.g., synthetic medical image 206) that is an augmentation of the parameterized synthetic image data based on the reference medical image. For example, the augmentation may cause the parametrized synthetic image data to be more realistic and/or closer in style to the reference medical image.

In step 680, method 670 may include storing the synthetic medical image in one or more data stores (e.g., in storage devices 109) for subsequent use in training or performance evaluation, for example.

FIG. 6F is a conceptual diagram 690 illustrating generation of a synthetic image using trained generative model 606 in accordance with method 640 described above in FIG. 6E. For example, at process 692, graphics simulator 602 may generate, from a real medical image having the specific data type included in the request received in step 672 of method 670, parameterized synthetic image data 694 corresponding to the requested data type. Parameterized synthetic image data 694 may then be provided as input to trained generative model 606 along with reference medical image 695 (e.g., received in step 672 of method 670). A predicted real medical image (e.g., predicted image 698) that corresponds to parameterized synthetic image data 694 and is augmented based on the reference medical image 695 may generated and output as part of inference process 696. Resultantly, predicted image 698 may be synthetic medical image (e.g., synthetic medical image 206) provided as output of the image generation process.

Augmenting Gleason Pattern 5 for Prostate Cancer Using Simulated Images and Conditional Generative Methods One form of severe prostate cancer contains significant quantities of Gleason Pattern 5, which indicates a poor outcome for the patient. However, severe prostate cancer patients are uncommon, in part due to early detection, resulting in limited amounts of image date available for training. Aspects described herein may be used to generate additional image data by creating new Gleason Pattern 5 images.

Composition-Based Methods for Generating Synthetic Image Data

Another method for generating synthetic images may include composition. Using a composition-based method, a synthetic example of an image or image region, containing a signal (e.g., a characteristic, data type, etc.), is composed with another image that does not contain a particular signal. For example, an image containing a rare morphology (e.g., a rare form of cancer or high grade of cancer) may be injected into or merged with another image without the cancer. As another example, artifacts may be injected (e.g., hair, bubbles, etc. in digital pathology slides) into an image that does not have them. Composition based methods may not require training, which may reduce computational and storage resources. While the synthetic images generated using these methods may not be visually appealing to humans making them less favorable than other methods described herein for generating synthetic images for training medical professionals, the visual appeal does not impact training of a machine learning system to improve a performance thereof.

FIG. 7 is a flowchart illustrating an exemplary method 700 for generating a synthetic image using composition methods. Exemplary method 700 may be performed (e.g., steps 702-710) by image synthesis tool 101 automatically or in response to a request from a user (e.g., physician, pathologist, etc.).

In step 702, method 700 may include receiving a request for a medical image having a data type (e.g., request 202). In step 704, method 700 may include retrieving, from a plurality of medical images stored in a data store (e.g., in storage devices 109), a first medical image having the requested data type. In some examples, a semantic segmentation annotation may be received for the first medical image that is associated with a region of the first medical image.

In step 706, method 700 may include retrieving, from the plurality of medical images, a second medical image without the requested data type. In some examples, the second medical image may one of the reference medical images provided as supplementary data (e.g., supplementary data 208). In some examples, the second medical image may be selected randomly from the medical images. In other examples, the second medical image may be selected from the medical images based on one or more features of the second medical image being complementary to one or more corresponding features of the first medical image.

In step 708, method 700 may include generating a synthetic medical image having the requested data type (e.g., synthetic medical image 206) using the first medical image and the second medical image. Various methods may be used to generate the synthetic medical image.

According to one aspect, the synthetic medical image may be generated by merging the first and second medical images. For example, the first medical image and the second medical image may be arranged side by side. One or more of the first medical image and the second medical image may be rotated to achieve alignment, if needed. Additionally or alternatively, one or more image properties of the first medical image and the second medical image (e.g., low-level image statistics such as color, brightness, etc.) may be matched. Once the first and second medical images are arranged, rotationally aligned, and/or property matched, the first medical image and the second medical image may be merged to generate the synthetic medical image.

According to another aspect, if the semantic segmentation associated with the region of the first medical image is received, the region may be identified and extracted from the first medical image based on the semantic segmentation annotation. The region may then be injected into the second medical image to generate the synthetic medical image.

In step 710, method 700 may include storing the synthetic medical image in one or more data stores (e.g., in storage devices 109) for subsequent use in training or performance evaluation, for example. The synthetic medical image may be stored in association with the requested data type.

Creating New Mucinous Breast Cancer Images Using Composition Methods

Some forms of breast cancer are relatively rare compared to others. For example, mucinous breast cancer occurs less than 5%, making it difficult to train machine learning systems that perform well on mucinous cancer. This invention can be used to create more mucinous cancer examples. For example, with an annotation on mucinous images the mucinous cancer region can be extracted from the image and injected into a benign breast image.

Figure 8:
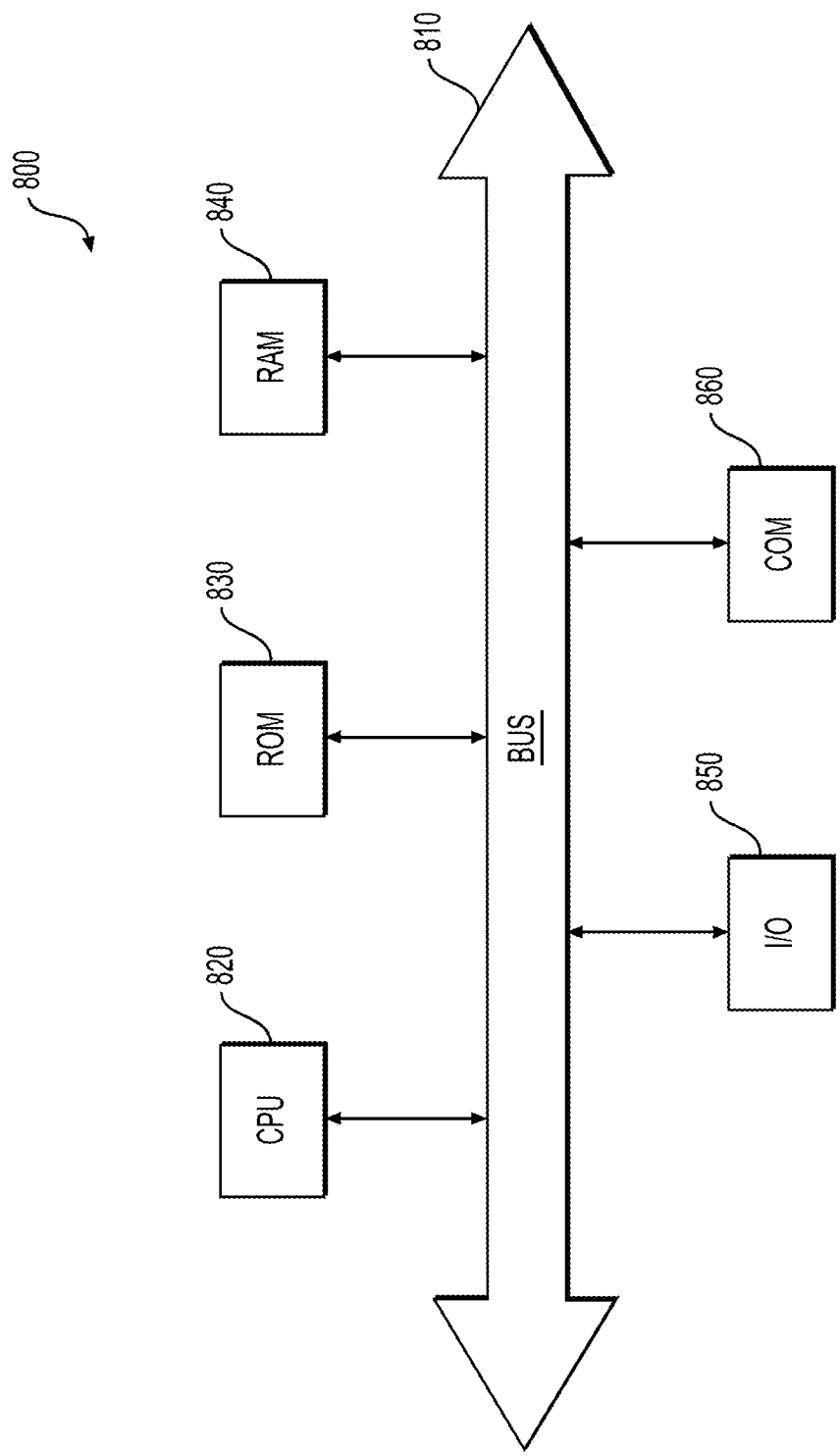
FIG. 8 depicts an exemplary system that may execute techniques presented herein.

FIG. 8 illustrates an example system or device 800 that may execute techniques presented herein. Device 800 may include a central processing unit (CPU) 820. CPU 820 may be any type of processor device including, for example, any type of special purpose or a general-purpose microprocessor device. As will be appreciated by persons skilled in the relevant art, CPU 820 also may be a single processor in a multi-core/multiprocessor system, such system operating alone, or in a cluster of computing devices operating in a cluster or server farm. CPU 820 may be connected to a data communication infrastructure 810, for example a bus, message queue, network, or multi-core message-passing scheme.

Device 800 may also include a main memory 840, for example, random access memory (RAM), and also may include a secondary memory 830. Secondary memory 830, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 830 may include similar means for allowing computer programs or other instructions to be loaded into device 800. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 800.

Device 800 also may include a communications interface ("COM") 860. Communications interface 860 allows software and data to be transferred between device 800 and external devices. Communications interface 860 may include a modem, a network interface (such as an Ethernet card), a communications port, a PCMCIA slot and card, or the like. Software and data transferred via communications interface 860 may be in the form of signals, which may be electronic, electromagnetic, optical or other signals capable of being received by communications interface 860. These signals may be provided to communications interface 860 via a communications path of device 800, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 800 may also include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other aspects may be apparent to those skilled in the art from consideration of the specification and practice of the invention disclosed herein. It is intended that the specification and examples be considered as exemplary only.

What is claimed is:

1. A system for composing a synthetic medical image, the system comprising:
   a data store for storing a plurality of medical images associated with data types;
   a processor; and
   a memory coupled to the processor and storing instructions that, when executed by the processor, cause the processor to perform operations including:
     receiving a request for a medical image having a data type;
     retrieving, from the plurality of medical images stored in the data store, a first medical image having the requested data type;
     retrieving, from the plurality of medical images stored in the data store, a second medical image without the requested data type;
     generating a synthetic medical image having the requested data type using the first medical image and the second medical image; and
     storing the synthetic medical image in association with the requested data type in the data store.

2. The system of claim 1, wherein generating the synthetic medical image includes:
   arranging the first medical image and the second medical image side by side;
   at least one of:
     rotationally aligning the first medical image and the second medical image; or
     matching one or more image properties of the first medical image and the second medical image; and
   merging the first medical image and the second medical image to generate the synthetic medical image.

3. The system of claim 1, the operations further including:
   receiving a semantic segmentation annotation for the first medical image associated with a region of the first medical image.

4. The system of claim 3, wherein generating the synthetic medical image includes:
   identifying the region of the first medical image based on the semantic segmentation annotation;
   extracting the region from the first medical image; and
   injecting the region into the second medical image to generate the synthetic medical image.

5. The system of claim 1, wherein the second medical image is selected randomly from the plurality of medical images for retrieval.

6. The system of claim 1, wherein the second medical image is selected from the plurality of medical images for retrieval based on one or more features of the second medical image being complementary to one or more corresponding features of the first medical image.

7. The system of claim 1, the operations further including:
   providing at least a portion of the plurality of medical images stored in the data store, including the synthetic medical image, and corresponding labels identifying the associated data types as a training dataset for input to a machine learning system to train the machine learning system.

8. The system of claim 1, wherein the requested data type includes at least one of: an image modality, a target anatomical region, a target morphology, a presence or absence of a condition, or a presence or absence of a treatment effect.

9. The system of claim 8, wherein the image modality includes digital pathology, magnetic resonance imaging (MRI), computed tomography (CT), X-ray, nuclear medicine imaging, or ultrasound.

10. The system of claim 8, wherein at least one of the target morphology, the condition, or the treatment effect included in the requested data type is a rare presentation below a predetermined threshold of occurrence.

11. A method to compose a synthetic medical image, the method comprising:
    receiving a request for a medical image having a data type;
    retrieving, from a data store storing a plurality of medical images associated with data types, a first medical image having the requested data type;
    retrieving, from the data store, a second medical image without the requested data type;
    generating a synthetic medical image having the requested data type using the first medical image and the second medical image; and
    storing the synthetic medical image in association with the requested data type in the data store.

12. The method of claim 11, wherein generating the synthetic medical image comprises:
    arranging the first medical image and the second medical image side by side;
    at least one of:
      rotationally aligning the first medical image and the second medical image; or
      matching one or more image properties of the first medical image and the second medical image; and
    merging the first medical image and the second medical image to generate the synthetic medical image.

13. The method of claim 11, further comprising:
    receiving a semantic segmentation annotation for the first medical image associated with a region of the first medical image.

14. The method of claim 13, wherein generating the synthetic medical image comprises:
    identifying the region of the first medical image based on the semantic segmentation annotation;
    extracting the region from the first medical image; and
    injecting the region into the second medical image to generate the synthetic medical image.

15. The method of claim 11, wherein retrieving the second medical image comprises:
    randomly selecting the second medical image from the plurality of medical images stored in the data store.

16. The method of claim 11, wherein retrieving the second medical image comprises:

selecting the second medical image from the plurality of medical images stored in the data store based on one or more features of the second medical image being complementary to one or more corresponding features of the first medical image.

17. The method of claim 11, further comprising:
providing at least a portion of the plurality of the medical images stored in the data store, including the synthetic medical image, and corresponding labels identifying the associated data types as a training dataset for input to a machine learning system to train the machine learning system.

18. The method of claim 11, wherein the requested data type includes at least one of: an image modality, a target anatomical region, a target morphology, a presence or absence of a condition, or a presence or absence of a treatment effect.

19. The method of claim 18, wherein at least one of the target morphology, the condition, or the treatment effect included in the requested data type is a rare presentation below a predetermined threshold of occurrence.

20. A non-transitory computer-readable medium storing instructions that, when executed by a processor, cause the processor to perform operations for composing a synthetic medical image, the operations comprising:
receiving a request for a medical image having a data type;
retrieving, from a data store storing a plurality of medical images associated with data types, a first medical image having the requested data type;
retrieving, from the data store, a second medical image without the requested data type;
generating a synthetic medical image having the requested data type using the first medical image and the second medical image; and
storing the synthetic medical image in association with the requested data type in the data store.

* * * * *